(12) United States Patent
Hostetter et al.

(10) Patent No.: US 6,291,654 B1
(45) Date of Patent: Sep. 18, 2001

(54) **METHOD FOR ISOLATING A C3 BINDING PROTEIN OF *STREPTOCOCCUS PNEUMONIAE***

(75) Inventors: Margaret K. Hostetter, New Haven, CT (US); Qi Cheng, Plymouth, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/308,022

(22) PCT Filed: Nov. 12, 1997

(86) PCT No.: PCT/US97/20586

§ 371 Date: May 12, 1999

§ 102(e) Date: May 12, 1999

(87) PCT Pub. No.: WO98/21337

PCT Pub. Date: May 22, 1998

Related U.S. Application Data

(60) Provisional application No. 60/062,473, filed on Oct. 16, 1997, provisional application No. 60/059,368, filed on Sep. 19, 1997, provisional application No. 60/038,086, filed on Feb. 18, 1997, and provisional application No. 60/029,444, filed on Nov. 12, 1996.

(51) Int. Cl.$^7$ ........................................ C07K 1/14

(52) U.S. Cl. ..................... 530/413; 530/412; 530/422; 530/424

(58) Field of Search .................. 530/412, 413, 530/415, 424

(56) References Cited

U.S. PATENT DOCUMENTS

| | | |
|---|---|---|
| 5,476,929 | 12/1995 | Briles et al. . |
| 5,510,264 | 4/1996 | Van Alstyne et al. . |

FOREIGN PATENT DOCUMENTS

| | | |
|---|---|---|
| 0 622 081 A2 | 11/1994 | (EP) . |
| WO 93/24000 | 12/1993 | (WO) . |
| WO 95/06732 | 3/1995 | (WO) . |
| WO 97/41151 | 11/1997 | (WO) . |
| WO 98/21337 | 5/1998 | (WO) . |

OTHER PUBLICATIONS

Cheng et al., "A C–3 binding protein in *Streptococcus pneumoniae*," Abstract B–478, p. 110, Abstracts of the 97$^{th}$ Annual Meeting of the American Society for Microbiology, Miami Beach, (May 4–8, 1997).

Hostetter, "Opsonic and Nonopsonic Interactions of C3 with *Streptococcus pneumoniae*," *Microbial Drug Resistance*, 5(2):85–89 (1999).

Madsen et al., "Production of IL–8 by Pulmonary Epithelial Cells in Response to Secreted Proteins of *S. pneumoniae*," Abstract 736, *Pediatr. Res.* 41(4, part 2):125A (1997).

Smith et al., "Characterization of a Pneumococcal Surface Protein that Binds Complement Protein C3 and its Role in Adhesion," 98$^{th}$ General Meeting of the American Society for Microbiology, Atlanta, May 17–21, 1998, Abstract D–122, *Abstracts of the General Meeting of the American Society for Microbiology*, p. 233 (1998).

Cannon et al., "Immunogenicity of C3 Binding Protein of *Streptococcus pneumoniae*," Abstract and Poster, MARC/MBRS National Meeting, Miami (Nov. 13–17, 1996).

Agrawal et al., "Probing the Phosphocholine–binding Site of Human C–reactive Protein by Site–directed Mutagenesis," *J. Biol. Chem.* 267:25352–25358 (1992).

Angel et al., "Degradation of C3 by *Streptococcus pneumoniae*," *The Journal of Infect. Diseases*, 170:600–608 (1994).

Baquero et al., "A review of antibiotic resistance patterns of *Streptococcus pneumoniae* in Europe," *J. Antimicrob. Chemother.*, 28(Suppl. C):31–38 (1991).

Berry et al., "Cloning and Nucleotide Sequence of the *Streptococcus pneumoniae* Hyaluronidase Gene and Purification of the Enzyme from Recombinant *Escherichia coli*," *Infect. Immun.*, 62:1101–1108 (1994).

Bohnsack et al., "Purification of the proteinase from group B streptococci that inactivates human C5a," *Biochim. et Biophys. Acta.*, 1079:222–228 (1991).

Charriaut–Marlangue et al., "Identification of P–57, a Serine Proteinase, From Human Erythocyte Membranes, Which Cleaves Both Chains of the Human Third Component (C3) of Complement," *Biochem. Biophys. Res. Commun.*, 140:1113–1120 (1986).

Cleary et al., "Similarity between the Group B and A Streptococcal C5a Peptidase Genes," *Infect. Immun.*, 60:4239–4244 (1992).

Connor et al., "Human Immunodeficiency Virus Infections in Infants and Children," *Current Topics in AIDS*, 1:185–209 (1987).

Cundell et al., "Peptide Permeases from *Streptococcus pneumoniae* Affect Adherence to Eucaryotic Cells," *Infect. Immun.*, 63:2493–2498 (1995).

Du Clos et al., "Definition of a C–reactive Protein Binding Determinant on Histones," *J. Biol. Chem.*, 266:2167–2171 (1991).

(List continued on next page.)

Primary Examiner—Donna C. Wortman
Assistant Examiner—Robert A. Zeman
(74) *Attorney, Agent, or Firm*—Mueting, Raasch & Gebhardt, P.A.

(57) ABSTRACT

This invention relates to the identification of a human complement C3 binding protein from *Streptococcus pneumoniae* and to its sequence and to methods for its purification and use. The protein binds but does not degrade or cleave C3 and is implicated in *S. pneumoniae* virulence. The protein is recognized by antibodies produced by humans recovering from pneumococcal infection.

5 Claims, 7 Drawing Sheets

OTHER PUBLICATIONS

Figure 3A:
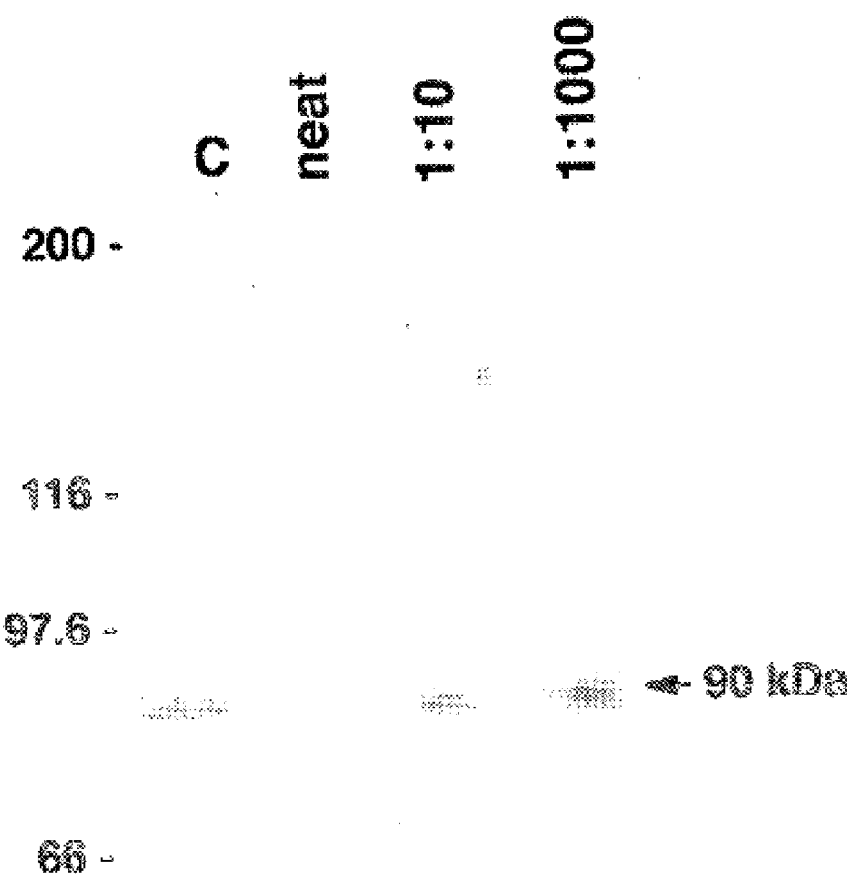

Giebink et al., "Pneumococcal Capsular Polysaccharide–Meningococcal Outer Membrane Protein Complex Conjugate Vaccines: Immunogenicity and Efficacy in Experimental Pneumococcal Otitis Media," *J. Infect. Dis.*, 167:347–355 (1993).

Gordon et al., "Characteristics of iC3b binding to human polymorphonuclear leucocytes," *Immunology*, 60:553–558 (1987).

Gordon et al., "Ligand–Receptor Interactions in the Phagocytosis of Virulent *Streptococcus pneumoniae* by Polymorphonulcear Leukocytes," *J. Infect. Dis.*, 154:619–626 (1986).

Hammerschmidt, et al., "SpsA, a novel pneumococcal surface protein with specific binding to secretory Immunoglobulin A and secretory component," *Molecular Microbiology*, 25:1113–1124 (1997).

Hammerschmidt, et al., "SpsA, a novel pneumococcal surface protein with specific binding to secretory Immunoglobulin A and secretory component," *EMBL Sequence Database*, Accession No. AJ002054 (1997).

Harlow et al., *Antibodies: a Laboratory Manual*, Cold Spring Harbor, NY; Cold Spring Harbor Laboratory Press, 473–510 (1988).

Havarstein et al., "An unmodified heptadecapeptide pheromone induces competence for genetic transformation in *Streptococcus pneumoniae*," *Proc. Natl. Acad. Sci.* (USA), 92:11140–11144 (1995).

Henwick et al., "Specificity of three anti–complement factor 3 monoclonal antibodies," *J. Immunol. Meth.*, 153:173–184 (1992).

Hostetter et al., "The Biochemistry of Opsonization: Central Role of the Reactive Thiolester of the Third Component of Complement," *J. Infect. Dis.*, 150:653–661 (1984).

Hostetter, "C3 Binding by *Streptococcus pneumoniae*: Opsonic and Non–Opsonic Deposition," *International Workshop—Streptococcus pneumoniae: Molecular Biology and Mechanisms of Disease– Update for the 1990's.* 2pp., (Sep. 23–29 1996).

Hostetter et al., "Biochemistry of C3 and Related Thiolester Proteins in Infection and Inflammation," *Rev. Infect. Dis.*, 9:97–109 (1987).

Hostetter, "C3 and C4 as opsonins in natural immunity," *The Natural Immune System—Humoral Factors*, ed. E. Sim, IRL Press, Oxford University, New York, pp. 177–208.

Hostetter et al., "Binding of C3b proceeds by a transesterification reaction at the thioloester site," *Nature*, 298:72–75 (1982).

Janoff et al., "Pneumococcal Disease during HIV Infection. Epidemiologic, Clinical, and Immunologic Perspectives," *Ann. Intern. Med.*, 117:314–324 (1992).

Jasin, "Human Heat Labile Opsonins: Evidence for Their Mediation Via the Alternative Pathway of Complement Activation," *J. Immunol.*, 109:26–31 (1972).

Johnston et al., "The Enhancement of Bacterial Phagocytosis by Serum," *J. Exp. Med.*, 129:1275–1290 (1969).

Lee et al., "Protection of infant mice from challenge with *Streptococcus pneumoniae* type 19F by immunization with a type 19F polysaccharide—pneumolysoid conjugate," *Vaccine*, 12:875–878 (1994).

Liu et al., "A Phosphocholine–Binding Protein from Limulus Amebocytes with Adhesion–Promoting Properties," *J. Biol Chem.*, 266:14813–14821 (1991).

Macrina et al., "Novel shuttle plasmid vehicles for Escherichia–Streptococcus transgeneric cloning," *Gene*, 25:145–150 (1983).

McDaniel et al.,"Localization of protection–eliciting epitopes on PspA of *Streptococcus pneumoniae* between amino acid residues 192 and 260," *Microb. Pathogen.*, 17:323–337 (1994).

McDaniel et al., "Molecular localization of variable and conserved regions of pspA and identification of additional pspA homologous sequences in *Streptococcus pneumoniae*," *Microb. Pathogen.*, 13:261–269 (1992).

Michael et al., "Expression of CD21 and synthesis of its ligands by HeLa cells after growth in serum–free medium," *J. Lab. Clin. Med.*, 125:102–112 (1995).

Nandiwada et al., Genetic Analysis of C3 Degrading Proteinase in *Streptococcus pneumoniae*, Abstracts, $96^{th}$ General Meeting of the American Society for Microbiology, May 19–23, 1996, New Orleans Louisiana, p. 177, Abstract No. B–134.

Ollert et al., "C3–Cleaving Membrane Proteinase, A New Complement Regulatory Protein of Human Melanoma Cells," *J. Immunology.*, 144:3862–3867 (1990).

Reed et al., "Cleavage of C3 by a Neutral Cysteine Proteinase of *Entamoeba histolytica*," *J. Immunol.*, 143:189–195 (1989).

Rosenow et al., "A family of immunogenic choline binding proteins decorate the surface of *Streptococcus pneumoniae* and block adherence to type II lung cells and endothelial cells of the peripheral vasculature,"*Abstracts, $96^{th}$ General Meeting of the American Society for Microbiology*, May 19–23, 1996, New Orleans Louisiana, p. 216, Abstract No. B–354.

Rosenow et al., "Contribution of novel choline–binding proteins to adherence, colonization and immunogenicity of *Streptococcus pneumoniae*," *Molecular Microbiology*, 25:819–829 (1997).

Rosenow et al., "Contribution of novel choline–binding proteins to adherence, colonization and immunogenicity of *Streptococcus pneumoniae*," *EMBL Sequence Database*, Accession No. AF019904 (1997).

Sambrook et al., *Molecular Cloning, A Laboratory Manual* Cold Spring Harbor Laboratory Press, Cold Spring Harbor, NY (1989) (Title Page, Copyright Page, and Table of Contents).

Sampson et al., "Cloning and Nucleotide Sequence Analysis of psA, the *Streptococcus pneumoniae* Gene Encoding a 37–Kilodalton Protein Homologous to Previously Reported Streptococcus sp. Adhesins," *Infect. Immun.*, 62:319–324 (1994).

Shrive et al., "Three dimensional structure of human C–reactive protein," *Nature Structural Biology*, 3:346–354 (1996).

Sicard, "A New Synthetic Medium for Diplococcus Pneumoniae, and its Use for the Study of Reciprocal Transformation at the amiA Locus," *Genetics*, 50:31–44 (1964).

Smith et al., "Factors modulating pneumococcal adhesion," *Pediatr. Res.*, 39:185A Abstract No. 1097 (1996).

Suter et al., "Granulocyte Neutral Proteases and Pseudomonas Elastase as Possible Causes of Airway Damage in Patients with Cystic Fibrosis," *J. Infect. Dis.*, 149:523–531 (1984).

Wani et al., "Identification, Cloning, and Sequencing of the Immunoglobulin A1 Protease Gene of *Streptococcus pneumoniae*," *Infect. Immun.*, 64:3967–3974 (1996).

Yother et al., "Structural Properties and Evolutionary Relationships of PspA, a Surface Protein of *Streptoccous pneumoniae*, as Revealed by Sequence Analysis," *J. Bacteriol.*, 174:601–609 (1992).

Yother et al., "Novel Surface Attachment Mechanism of the *Streptococcus pneumoniae* Protein PspA," *J. Bacteriol.*, 176:2976–2985 (1994).

Zach et al., "Effect of Glucocorticoids on C3 Gene Expression by the A549 Human Pulmonary Epithelial Cell Line," *J. Immunol.*, 148:3964–3969 (1992).

```
                                                              50
1200        DRWKQENGMW   YFYNTDGSMA   TGWLQNNGSW   YYLNANGAMA   TGWLQNNGSW
r6x         ---KQENGMW   YFYNTDGSMA   TGWLQNNGSW   YYLNANGAMA   TGWLQNNGSW
23f         ---LETRNGMW  YFYNTDGSMA   TGWLQNNGSW   YYLNSNGAMA   TGWLQNNGSW 100
1200        YYLNANGSMA   TGWLQNNGSW   YYLNANGAMA   YYLNSNGAMA   TGWLQNNGSW
r6x         YYLNANGSMA   TGWLQYNGSW   YYLNANGAMA   YYLNSNGAMA   TGWLQNNGSW
23f         YYLNANGSMA   TGWLQNNGSW   YYLNSNGSMA   YYLNANGDMA   TGWLQNNGSW 150
1200        TGWLQYNGSW   YYLNANGDMA   TG*LQYNGSW   YYLNANGDMA   TGWLQNNGSW
r6x         TGWLQYNGSW   YYLNANGDMA   TGWLQYNGSW   YYLNANGDMA   TGWLQNNGSW
23f         TGWLQNNGSW   YYLNANGSMA   TGWLQYNGSW   YYLNANGDMA   TGWLQNNGSW 200
1200        YYLNANGDMA   TGWVKDGDTW   YYLEASGAMK   ASQWFKVSDK   WYYVNGSGAL
r6x         YYLNANGDMA   TGWVKDGDTW   YYLEASGAMK   ASQWFKVSDK   WYYVNGSGAL
23F         YYLNANGDME   TGWVKDGDTW   YYLEASGAMK   ASQWFKVSDK   WYYVNGSGAL 223
1200        AVNTTVDGYG   VNANGEW*TK   H*Y
r6x         AVNTTVDGYG   VNANGEW*TK   P--
23f         AVNTTVDGYG   VNANGEW*TK   PNI
```

Fig. 1

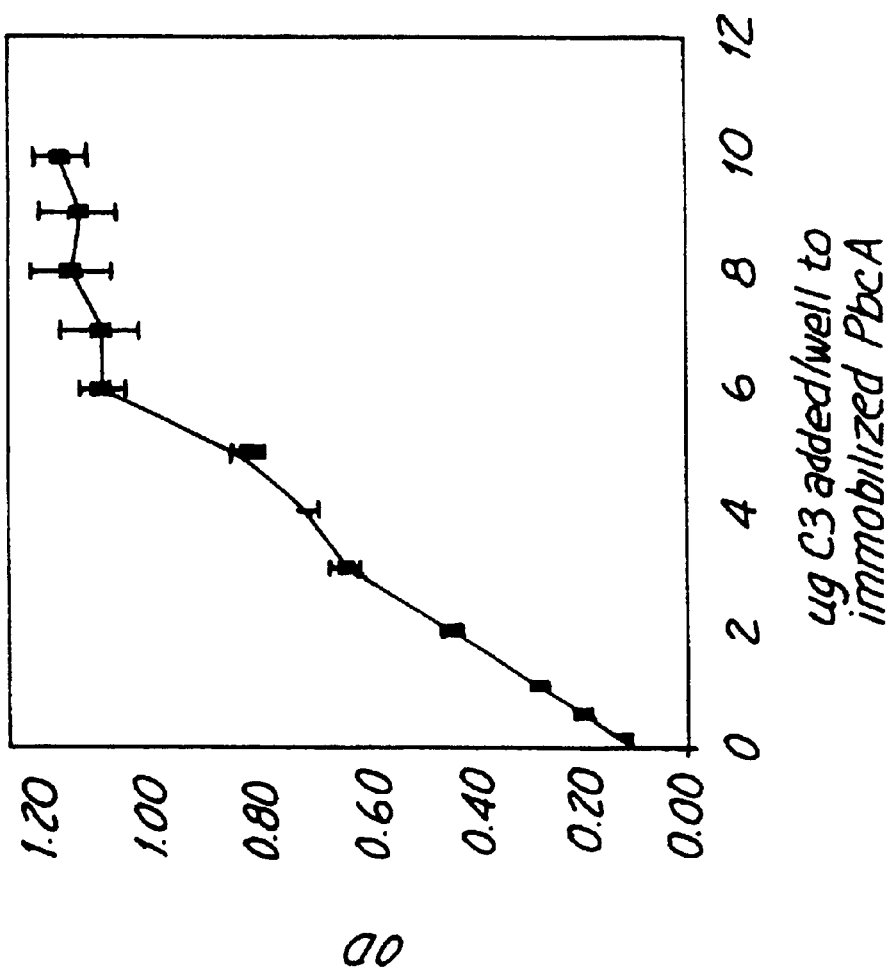

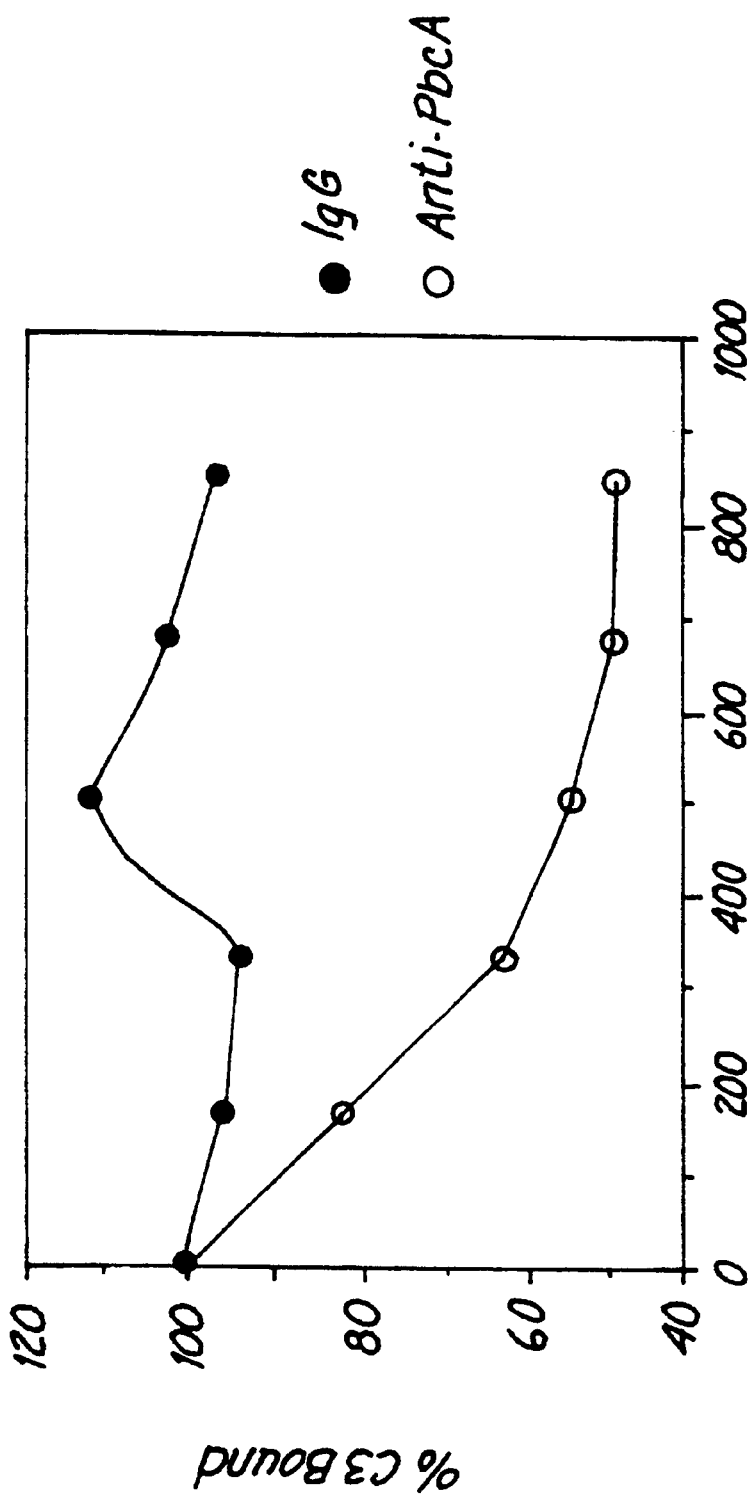

Insertion-duplication mutagenesis

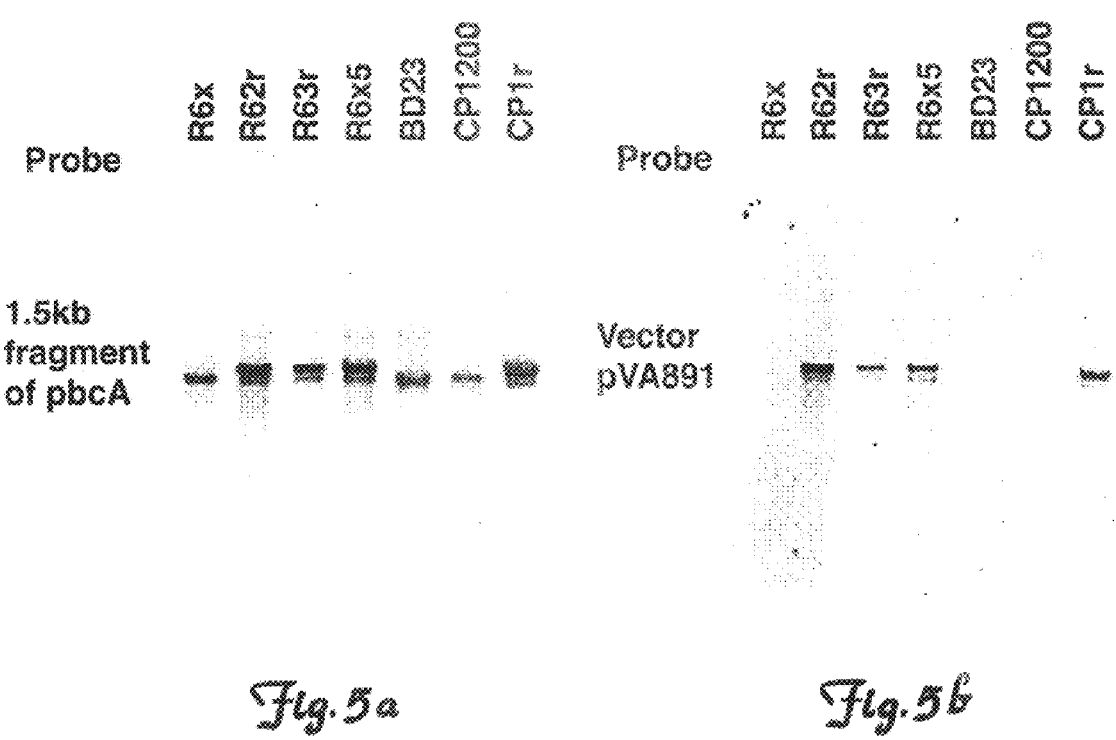

METHOD FOR ISOLATING A C3 BINDING PROTEIN OF *STREPTOCOCCUS PNEUMONIAE*

CROSS-REFERENCE TO RELATED APPLICATIONS

This application is a national stage application of PCT/US97/20586, filed Nov. 12, 1997, which claims the benefit of U.S. Provisional Patent Application Nos. 60/029,444 filed Nov. 12, 1996; 60/038,086 filed Feb. 18, 1997; 60/059,368 filed Sep. 19, 1997; and 60/062,473 filed Oct. 16, 1997.

FIELD OF THE INVENTION

This invention relates to *Streptococcus pneumoniae* and in particular this invention relates to the identification of an *S. pneumoniae* protein that is implicated in *S. pneumoniae* virulence and is capable of binding the complement protein, C3.

BACKGROUND OF THE INVENTION

Respiratory infection with the bacterium *Streptococcus pneumoniae* (*S. pneumoniae*) leads to an estimated 500,000 cases of pneumonia idand 47,000 deaths armually. Those persons at highest risk of bacteremic pneumococcal infection are infants under two years of age and therelderly. In these populations, *S. pneumoniae* is the leading cause of bacterial pneumonia and meningitis. Moreover, *S. pneumoniae* is the major bacterial cause of ear infections in children of all ages. Both children and the elderly share defects in the synthesis of protective antibodies to pneumococcal capsular polysaccharide after either bacterial colonization, local or systemic infection, or vaccination with purified polysaccharides. *S. pneumoniae* is the leading cause of invasive bacterial respiratory disease in both adults and children with HIV infection and produces hematogenous infection in these patients (Connor et al. *Current Topics in AIDS* 1987;1:185–209 and Janoffet al. *Ann. Intern. Med.* 1992;1 17(4):314–324).

Individuals who demonstrate the greatest risk for severe infection are not able to make antibodies to the current capsular polysaccharide vaccines. As a result, there are now four conjugate vaccines in clinical trial. Conjugate vaccines consist of pneumococcal capsular polysaccharides coupled to protein carriers or adjuvants in an attempt to boost the antibody response. However, there are other potential problems with conjugate vaccines currently in clinical trials. For example, pneumococcal serotypes that are most prevalent in the United States are different from the serotypes that are most common in places such as Israel, Western Europe, or Scandinavia. Therefore, vaccines that may be useful in one geographic locale may not be useful in another. The potential need to modify currently available capsular polysaccharide vaccines or to develop protein conjugates for capsular vaccines to suit geographic serotype variability entails prohibitive financial and technical complications. Thus, the search for immunogenic, surface-exposed proteins that are conserved worldwide among a variety of virulent serotypes is of prime importance to the prevention of pneumococcal infection and to the formulation of broadly protective pneumococcal vaccines. Moreover, the emergence of penicillin and cephalosporin-resistant pneumococci on a worldwide basis makes the need for effective vaccines even more exigent (Baquero et al. *J. Antimicrob. Chemother.* 1991;28S;31–8).

Several pneumococcal proteins have been proposed for conjugation to pneumococcal capsular polysaccharide or as single immunogens to stimulate immunity against *S. pneumoniae*. Surface proteins that are reported to be involved in adhesion of *S. pneumoniae* to epithelial cells of the respiratory tract include PsaA, PspC/CBP112, and IgA1 proteinase (Sampson et al. *Infect. Immun.* 1994;62:319–324, Sheffield et al. *Microb. Pathogen.* 1992; 13: 261–9, and Wani. et al. *Infect. Immun.* 1996; 64:3967–3974). Antibodies to these adhesins could inhibit binding of pneumococci to respiratory epithelial cells and thereby reduce colonization. Other cytosolic pneumococcal proteins such as pneumolysin, autolysin, neuraninidase, or hyaluronidase are proposed as vaccine antigens because antibodies could potentially block the toxic effects of these proteins in patients infected with *S. pneumoniae*. However, these proteins are typically not located on the surface of *S. pneumoniae*, rather they are secreted or released from the bacterium as the cells lyse and die (Lee et al. *Vaccine* 1994; 12:875–8 and Berry et al. *Infect Immun.* 1994; 62:1101–1108). While use of these cytosolic proteins as immunogens might ameliorate late consequences of *S. pneumoniae* infection, antibodies to these proteins would neither promote pneumococcal death nor prevent pneumococcal colonization.

A prototypic surface protein that is being tested as a pneumococcal vaccine is the pneumococcal surface protein A (PspA). PspA is a heterogeneous protein of about 70–140 kDa. The PspA structure includes an alpha helix at the amino terminus, a proline-rich sequence in the mid-portion of the protein. and terminates in a series of choline-binding repeats at the carboxy-terminus. Although much information regarding its structure is available PspA is not structurally conserved among a variety of pneumococcal serotypes, and its fanction is entirely unknown (Yother et al. *J. Bacteriol.* 1992;1 74:601–9 and Yother *J. Bacteriol.* 1994; 176:2976–2985). Studies have confirmed the immunogenicity of PspA in animals (McDaniel et al. *Microb. Pathogen.* 1994; 17:323–337). Despite the immunogenicity of PspA, the heterogeneity of PspA, its existence in four structural groups (or clades), and its uncharacterized function complicate its ability to be used as a vaccine antigen.

In patients who cannot make protective antibodies to the type-specific polysaccharide capsule, the third component of complement, C3, and the associated proteins of the alternative complement pathway constitute the first line of host defense against *S. pneumoniae* infection. Because complement proteins cannot penetrate the rigid cell wall of *S. pneumoniae*, deposition of opsonic C3b on the pneumococcal surface is the principal mediator of pneumococcal clearance. Interactions of pneumococci with plasma C3 are known to occur during pneurnococcal bacteremia, when the covalent binding of C3b, the opsonically active fragment of C3, initiates phagocytic recognition and ingestion (Johnston et al. *J. Exp. Med* 1969;129:1275–1290, Hasin HE, *J. Immunol.* 1972; 109:26–31 and Hostetter et al. *J. Infect. Dis.* 1984; 150:653–61). C3b deposits on the pneumococcal capsule, as well as on the cell wall. This method for controlling *S. pneumoniae* infection is fairly inefficient and could be beneficially amplified by the presence of antibodies to surface components of *S. pneumoniae*. There currently exists a strong need for methods and therapies to limit *S. pneumoniae* infection.

SUMMARY OF THE INVNETION

The present invention relates to the identification and purification of an about 90 kDa to about 110 kDa (±5 kDa) protein, as determined following electrophoresis on a 15% SDS-PAGE gel. The protein is named PbcA and is sisolatable from *S. pneumoniae* strains that are capable of binding to human complement protein C3. The protein, PbcA, comprises an amino terminus containing region comprising SEQ ID NO:1 and is capable of binding but not cleaving or degrading the human complement protein C3. The protein also comprises a proline rich region and in one embodiment is a surface exposed protein of S. pneumoniae.

This invention also relates to the production of antibodies specifically recognizing PbcA. In one embodiment the antibodies are polyclonal and in another embodiment the antibodies are monoclonal. The antibodies can be produced by immunizing a mammal with all or a portion of PbcA. In one embodiment, the monoclonal antibodies are rodent derived.

In another aspect of this invention a method is provided for generating an immune response to S. pneumoniae in vivo comprising the steps of: administering a protein or an immunogenic fragment of a protein from S. pneumoniae to an animal wherein the amino terminus containing region of the protein comprises SEQ ID NO:1. In one embodiment, the protein is capable of binding but not cleaving or degrading the human complement protein C3. Preferably, the method further comprises detecting an immune response to S. pneumoniae in the mammal. Preferably, the immune response comprises the production of antibodies to S. pneumoniae. The animal can be a mouse, rat, chinchilla, a rabbit or a human and the method can further comprise the steps of isolating antibody producing cells from the mammal and preparing monoclonal antibodies to the C3 binding protein.

In yet another aspect of the invention a method is disclosed for obtaining a purified C3 binding protein from S. pneumoniae comprising the steps of: obtaining a protein sample from S. pneumoniae; precipitating the protein to formn a precipitate; applying the precipitate to a Thiopropyl Sepharose 6B affinity chromatography column comprising methylamine-treated C3; and eluting the C3 binding protein from the column using an elution buffer comprising about 20% ethanol. In one aspect of this embodiment the invention relates to C3 binding protein preparable by these methods.

This invention also relates to a C3 binding protein having the sequence of SEQ ID NO:6 and to isolated nucleic acid encoding a C3 binding protein and comprising the DNA sequence of SEQ ID NO:5 and to isolated nucleic acid having the DNA sequence of SEQ ID NO:4.

In another aspect of this invention, the invention relates to isolated nucleic acid encoding C3 binding protein of about 90 kDa to about 110 kDa (±5 kDa), in one embodiment, and comprising nucleic acids 1–1500 of SEQ ID NO:5 and to an isolated nucleic acid sequence encoding the C3 binding protein wherein the protein exhibits C3 binding activity and wherein the protein comprises at least 80% nucleic acid homology to nucleic acids 1–1500 of SEQ ID NO:5. Preferably, the nucleic acid homology is at least 95%.

The invention also relates to a C3 binding protein isolatable from S. pneumoniae having DNA that is hybridizable to a nucleic acid fragment of at least 500 bp from nucleic acids 1–1500 of SEQ ID NO:5 under hybridization conditions of about 6×SSC, 5×Denhardt's, 0.5% SDS, 100 µg/ml denatured, fragment salmon sperrn DNA overnight at 65° C. and washed in 2×SSC, 0.1% SDS, one time at room temperature for about 10 mn, followed by one time at 65° C. for about 15 mn and followed by at least one wash in 0.2×SSC, 0.1% SDS at room temperature for about 3–5 minutes. Preferably this protein frher comprises at least 2 choline binding repeat and still more preferably the protein further comprises at least 2 choline binding repeats.

The invention also relates to peptide fragments of at least 15 bp from SEQ ID NO:5 and to insertion and deletion mutants that do not express PbcA.

In another aspect of this invention, the invention relates to PbcA proteins. In one embodiment the invention relates to an isolated protein comprising SEQ ID NO:1 and at least two choline binding repeats. Preferably the protein is isolated from S. pneumoniae and also preferably the protein binds human complement protein C3. in one version of this embodiment, the protein is a recombinant protein or a purified protein from S. pneumoniae. Preferably the protein has a molecular weight as determined on a 15% polyacrylamide gel of between about 90 kDa to about 110 kDa and preferably the protein comprises a proline rich region. Additionally the protein can comprise SEQ ID NO:2 or SEQ ID NO:3.

Alternatively, the protein of this invention can comprise SEQ ID NO:6 or the protein can be an isolated protein capable of binding to, but not cleaving or degrading, human complement C3 and wherein the protein comprises SEQ ID NO:1. Preferably the protein is isolated from S. pneumoniae and in one embodiment, the protein further comprises a proline rich region. The protein can flirther comprise SEQ ID NO:2. Preferably the protein has at least about 95% homology to a C3 binding protein from S. pneumoniae and also preferably, the protein has a molecular weight as determined on a 15% polyacrylamide gel of between about 90 kDa to about 110 kla. In one aspect, the isolated protein is a recombinant protein and in another, the protein is isolated from S. pneumoniae bacteria.

In another embodiment of the proteins of this invention, the invention relates to a recombinant protein comprising SEQ ID NO:1, wherein the protein has a molecular weight as determined on a 15% polyacrylamide gel of between about 90 kDa to about 110 kDa. Preferably the protein binds human complement protein C3. The protein can firher include a proline rich region and preferably the protein does not cleave or degrade human complement protein C3.

In another embodiment of the proteins of this invention, the protein comprises amino acids 1–410 of SEQ ID NO:6.

In yet another embodiment of the proteins of this invention, the invention relates to a protein that binds, but does not cleave or degrade. human complement protein C3, wherein nucleic acid encoding the protein hybridizes to SEQ ID NO:4 under hybridization conditions of 6×SSC, 5×Denhardt, 0.5% SDS, and 100 µg/ml fragmented and denatured salmon sperm DNA hybridized overnight at 65° C. and washed in 2×SSC, 0.1% SDS one time at room temperature for about 10 minutes followed by one time at, 65° C. for about 15 minutes followed by at least one wash in 0.2×SSC, 0.1% SDS at room temperature for at least 3–5 minutes. Preferably, the protein further comprises SEQ ID NO:1 and optionally, the protein can comprise SEQ ID NO:2 or SEQ ID NO:3. Preferably the protein is at least 15 amino acids in length. Preferably the protein comprises a proline rich region. In one aspect of this embodiment, the protein is a recombinant protein and in another, the protein is a synthetic peptide. In one aspect of this embodiment, the protein is a peptide of at least 15 amino acids from SEQ ID NO:6. The proteins can also be used to create antibody and the proteins of this embodiment can be used to generate antibody capable of specifically binding to the protein. In one embodiment, the antibody is a monoclonal antibody and in another the antibody is a polyclonal antibody. Preferably the monoclonal antibody is at least partially rodent-derived.

This invention also relates to nucleic acid encoding the proteins of this invention. In one embodiment, the nucleic acid of this invention encodes a protein comprising at least two choline binding domains and SEQ ID NO:1. Preferably the protein encoded by the nucleic acid further comprising a proline rich region. Also preferably, the nucleic acid is isolated from an *S. pneumoniae* genome. Preferably, the nucleic acid is capable of hybridizing to SEQ ID NO:4 and in another embodiment, the protein encoded by the nucleic acid binds to human complement protein C3. In one aspect of this embodiment, the nucleic acid ispositioned in a nucleic acid vector. Preferably the vector is an expression vector and the expression vector directs expression of the protein by the nucleic acid.

In another embodiment of the nucleic acid of this invention, the invention relates to isolated nucleic acid encoding a protein comprising SEQ ID NO:1 and a proline rich region wherein the protein encoded by the nucleic acid binds but does not cleave or degrade human complement C3.

In yet another embodiment, the invention relates to isolated nucleic acid fragment encoding an about 90 kDa to about 110 kDa protein with C3 binding activity, wherein the nucleic acid fragment has at least 80% homology to at least 500 bp from nucleic acids 1–1500 of SEQ ID NO:5 and in another embodiment, the isolated nucleic acid fragment comprises base pairs 1–1510 of SEQ ID NO:5.

The invention also relates to a method for isolating a C3 binding protein from a bacterium comprising the steps of: obtaining a protein sample from a bacterium; applying the sample to a solid support comprising methylamine treated complement protein C3; washing the solid support; and removing a C3 binding protein from the solid support in a solution comprising alcohol wherein the C3 binding protein does not cleave or degrade C3. Preferably the bacterium is *S. pneumoniae* and in another embodiment, the bacterium is *E. coli*. Preferably the solid support comprises an affinity column and preferably the alcohol is ethanol. In one embodiment, the solution comprising alcohol is a buffer comprising 20% ethanol. The invention also relates to C3 binding protein preparable by this method.

The invention also relates to a method for producing an immune response to *S. pneumoniae* comprising the steps of: administering a therapeutically effective amount of of at least a portion of a protein to a mammal, wherein the protein binds but does not cleave or degrade human complement protein C3 and, wherein nucleic acid encoding the protein hybridizes to SEQ ID NO:4 under hybridization conditions of 6×SSC, 5×Denhardt, 0.5% SDS, and 100 μg/ml fragmented and denatured salmon sperm DNA, hybridized overnight at 65° C. and washed in 2×SSC, 0.1% SDS one time at room temperature for about 10 minutes followed by one time at 65° C. for about 15 minutes followed by at least one wash in 0.2×SSC, 0.1% SDS at room temperature for at least 3–5 minutes; and detecting an immune response to the protein. In one embodiment, the protein is at least 15 amino acids in length and in another the protein is a chimeric protein. In yet another embodiment, the protein comprises SEQ ID NO:1. In another embodiment, the protein has a molecular weight on a 15% polyacrylamide gel of between about 90 kDa to about 110 lkDa.

The invention also relates to a method for reducing *S. pneumoniae* binding to C3 comprising the steps of: administering a therapeutically effective amount of at least a portion of an antibody to a mammal, wherein the antibody specifically recognizes a C3 binding protein from *S. pneumoniae*, and wherein the C3 binding protein is a protein that binds, but does not cleave or degrade human complement protein C3. In one embodiment the antibody comprises at least one variable domain from a monoclonal antibody. In another embodiment, the antibody is administered to the air passages of the mammal or intravenously.

In yet another aspect of this invention, the invention relates to a non-naturally occurring *S. pneumoniae* bacterium that does not express a detectable human complement C3 binding protein, wherein the C3 binding protein comprises SEQ ID NO: 1. In one embodiment. the bacterlum is the product of an insertion into the gene encoding the C3 binding protein and in another, the bacterium is a product of a deletion in the gene encoding the C3 binding protein. In yet another embodiment, the bacterium is produced by homologous recombination of the gene encoding the C3 binding protein gene with at least a portion of a non-native C3 binding protein gene and in one aspect of this embodiment, the gene encoding at least a portion of the non-native C3 binding protein comprises a mutation within the non-native gene.

BRIEF DESCRIPTION OF THE FIGURES

FIG. 1 is an amino acid alignment of the choline binding regions of PbcA from *S. pneumoniae* strais CP1200, R6x and 23F (SEQ ID NOS:9, 10, and11).

FIG. 2 is a graph illustrating PbcA binding to human C3 by ELISA.

FIG. 3 summarizes studies to assess the ability of antibody to PbcA to inhibit C3 binding. FIG. 3*a* is a Western blot illustrating the specificity of the antibody preparation for PbcA from CP1200. FIG. 3*b* is a graph illustrating the ability of antibody to PbcA to inhibit C3 binding by ELISA.

FIG. 4 illustrates an exemplary strategy for producing a pbcA insertion mutant.

FIG. 5*a* is a photograph of a Southern blot of DNA from transformed and nontransformed *S. pneumoniae* cells probed with a 1.5 kb fragment of pbcA. FIG. 5*b* is a photograph of a Southern blot probed with vector pVA891.

FIG. 6 is a photograph of Western blot experiments demonstrating that the insertion-duplication mutants of this invention do not produce PbcA protein capable of binding C3 or antibody to PbcA.

DETAILED DESCRIPTION OF THE PREFERRED EMBODIMENTS

The present invention provides a *S. pneumoniae* protein that binds C3. The protein is about 90 kDa to about 110 kDa (±about 5 kDa) in mass as observed following electrophoresis on a 15% SDS-PAGE gel and is referred to in this disclosure as "PbcA." PbcA was initially identified using the methods of Example 1. Supernatant proteins from exponentially growing cultures of *S. pneumoniae* were tested by Western blot for their ability to bind to purified human C3 following electrophoresis on a 15% SDS-PAGE gel. In the *S. pneumoniae* strain CP1200, both lysates and supernatants from exponentially growing cells produced a protein band, identified as PbcA, at approximately 90 kDa on 15% SDS-PAGE gels under non-reducing conditions. The protein bound methylamine-treated human C3 (produced as described by Hostetter MK, et al. *J. Inf. Dis*. 150:653–661, 1984), labeled with biotin. PbcA is present in lysates and supernatants from a variety of other *S. pneumoniae* strains. The size of PbcA varies on a 15% SDS-PAge gel in *S. pneumoniae* strains from about 90 kDa to about 110 kDa. All PbcA proteins identified thus far are capable of binding, but not cleaving or degrading, purified human complement protein C3. In some strains protein bands of smaller molecular weight are observed.

As will be recognized by those of skill in the art, there are a variety of methods for isolating an individual protein from bacterial supernatants. As one example, the *S. pneumoniae* C3 binding protein, PbcA, is isolated using the methods of Example 2. PbcA, can be purified from other secreted pneumococcal proteins by affinity chromatography. Secreted proteins can be precipitated in a final concentration of 10% trichloroacetic acid (TCA) at 4° C. overnight according to Example 2. Resuspended proteins from the TCA precipitate are subjected to affinity column chromatography using methylamine-treated human C3 (supra). Elution of the PbcA protein from the affinity column has proven to be difficult. Surprisingly, the PbcA protein from the column can be eluted using an elution buffer comprising an alcohol, preferably ethanol and more preferably about 20% ethanol in the Tris-HCl/NaCl wash buffer. In view of this disclosure, now that PbcA has been identified, those skilled in the art will recognize that other methods could be used to identify, isolate and purify the protein from a variety of C3-binding *S. pneumoniae* without undue experimentation.

Multiple eluates can be pooled to obtain sufficientsample for further analysis. As one example, a sample can be electrophoresed on an SDS-PAGE gel and transferred to nitrocellulose. The protein can be subjected to amino terminal analysis and tryptic digestion for internal peptide sequencing. The following sequences were obtained from the tryptic digest analysis:

A peptide positioned near the amino terminus:
TENEGSTQAATSSNMAKTEH (SEQ ID NO:1)
And internal regions:
EKPAEQPQPAPATQP (SEQ ID NO:2)
SSDSSVGEETLPSSSLK (SEQ ID NO:3)

SEQ ID NO:2 is proline rich and has at least a 75% homology with the *S. pneumoniae* protein PspA over 13 amino acids. Although the proline rich region of PspA aligned with SEQ ID NO:2, neither SEQ ID NO: 1 nor SEQ ID NO:3 had any substantial homology to any proteins or peptides previously published in the GenBank database (less than 35% homology). The term "proline rich" as used herein refers to a protein having a stretch of amino acids having at least 5 proline amino acids over a total of about 15 amino acids.

These sequences were confirmed in *S. pneumoniae* strain CP 1200 following isolation of the gene and sequencing to obtain the nucleic acid sequence encoding PbcA. In one embodiment of this invention, PbcA is an about 90 kDa to about 110 kDa (±5 kDa. meaning about 85 kDa to about 115 kDa) when *S. pneumoniae* proteins are separated on a 15% SDS-PAGE gel, and in another embodiment, the protein further includes SEQ ID NO:2 and SEQ ID NO:3.

Oligonucleotides corresponding in whole or in part to SEQ ID NOS: 1–3 are usefull for identifying and isolating the nucleic acid encoding PbcA (the gene encoding PbcA is termed pbcA) and for isolating the pbcA and PbcA from a variety of *S. pneumoniae* strains. For example, oligonucleotides corresponding in whole or in part from SEQ ID NOS 1–3 can be used to amplify sequences from genomic DNA isolated from *S. pneumoniae* using standard polymerase chain reaction technology. The amplified sequences can then be directly used as probes or the amplified sequences can be incorporated into a vector for plasmid amplification in a suitable host such as a bacteria or virus and then isolated for sequencing, cloning and for use as probes to detect DNA from libraries of *S. pneumoniae*. The DNA isolated from these procedures is useful in sequencing reactions to obtain the nucleic acid sequence encoding PbcA and to produce vectors, such as expression vectors encoding PbcA as well as for producing recombinant protein. Example 5 provides a preferred method for isolating nucleic acid encoding PbcA.

PbcA can be expressed as a recombinant protein or isolated from *S. pneumoniae* lysates. The *S. pneumoniae* C3 binding protein, PbcA, binds C3 without cleaving or degrading the C3 molecule. A number of bacterial proteins have been reported to bind and to cleave C3 or other complement proteins. For example, a 140 kDa C5a peptidase from group A streptococci cleaves a $His_{67}$-$Lys_{68}$ bond at the carboxy terminus of C5a, thereby abolishing the chemoattractant capabilities of the molecule. An enzyme related to the C5a peptidase is also found in group B streptococci (Cleary et al. *Infect. Immun.* 1992; 60:4239–4244 and Bohnsack et al. *Biochim. et Biophys. Acta* 1991; 1079:222–228). Production of an elastase-like enzyme, as can be seen with 24-hour culture supernatants from Pseudomonas aeruginosa (Suter et al. *J. Infect. Dis.* 1984; 149:523–31), cleaves C3 into characteristic fragments of 66 kDa and 100 kDa from the C3 α-chain. Like the elastase-like enzyme from *P. aeruginosa*, a 56 kDa neutral cysteine proteinase from *Entamoeba histolytica* cleaves C3a between residues $Ser_{78}$/$Asn_{79}$, yielding a defined C3 cleavage fragment of 105 kDa (Reed, et al. *J. Immunol.* 1989; 143:189–95).

C3-cleaving proteinases have been isolated from the membranes of some mammalian cells, including human erythrocytes (p57), neutrophils, and melanoma cells resistant to complement-mediated killing. These proteins are typically serine proteases which yield defined cleavage fragments. For example, p57 cleaves both the α- and β-chains of C3, while the melanoma proteinase cleaves only the α'-chain of C3b, generating a fragment of 35 kDa (Charriaut-Marlangue et al. *Biochem. Biophys. Res. Commun.* 1986; 140:1113–1120 and Ollert et al. *J. Immunol.* 1990; 144:3862–7).

In contrast to these studies, C3 cleavage and/or degradation was not observed with PbcA. PbcA binds C3 without the production of defined cleavage fragments and without evidence of degradation of C3. Although there are microbial precedents for binding and cleaving of complement proteins. there is no previously reported microbial protein that binds C3 non-covalently without degrading or cleaving the molecule. The interaction of C3 and other complement components with proteins from group A and B streptococci, *P. aeruginosa*, and amoebae appears to be quite distinct from what has been observed with *S. pneumoniae*.

Table 1 (SEQ ID NO:4) provides a nucleic acid sequence encompassing the open reading frame encoding a 90 kDa PbcA protein from *S. pneumoniae* strain CP1200. Untranslated 5' and 3' regions are also included in SEQ ID NO:4. The open reading frame encoding PbcA begins at nucleotide 383 and ends with nucleotide 2074. Table 2 is a map providing the amino acids (SEQ ID NO:6) encoded by the nucleic acids of the major open reading frame from SEQ ID NO:4 (provided in Table 2 as SEQ ID NO:5). The protein predicted from SEQ ID NO:4 contains an amino terminus containing segment with C3 binding activity (upstream from the choline binding repeat region) and a series of choline binding repeats (beginning in SEQ ID NO:5 at about nucleic acid position 1501).

Primers were selected from SEQ ID NO:4 to span the choline binding repeats to assess choline binding repeat variability between strains. The primers used were:

5' GCACAACCATCTACTCCA 3' (SEQ ID NO: 7), and
5' GTACAGGAATTCAGTATTAACTA 3' (SEQ ID NO:8)

Amplification reactions were performed using DNA from three different *S. pneumoniae* strains: CP1200, R6x and virulent strain 23F (obtained from Dr. Steve Pelton, Boston City Hospital, Boston, Mass. and identified as isolate "freezer #365"). The results of the amplification studies indicated that the number of choline binding repeats varied depending on the S. pneumoniae strain. For example, strain CP1200 contained about 4 repeats while 23F contained about 8 repeats and R6X contained at least about 10 choline binding repeats using the Yother et al. model for choline binding repeat regions (see infra). All S. pneumoniae strains studied thus far have at least two choline binding repeats. Therefore, in another embodiment of this invention, PbcA is a C3-binding protein from S. pneumoniae including SEQ ID NO:1 and at least 2 choline binding repeats.

Choline binding domains are known in the art and a number of references discuss the characteristics of a variety choline binding domains (see, for example, Du Clos et al. *J. Biol. Chem.* 266(4):2167–2171, 1991; Liu et al. *J. Biol. Chem.* 266(22):14813–14821, 1991; Agrawal et al. *J. Biol. Chem.* 267(35):25352–25358, 1992; and *Nature Structural Biology* 3(4):346–354, 1994). A choline-binding repeat sequence has been identified in S. pneumoniae protein PspA as TGWKQENGMWYFYNTDGSMA (SEQ ID NO:12) (see Yother, J. and White, J M, *J. Bacteriology* 176:2976–2985, 1994) Choline binding repeats are associated with membrane binding proteins. Without intending to limit this invention, the strains studied thus far indicate that the virulent strains appear to have more choline binding repeats on average than nonvirulent strains. At the very least it appears that S. pneumoniae strains show considerable variability in the choline binding repeat region.

These results are consistent with electrophoretic studies assessing variability in the size of PbcA proteins obtained from a number of S. pneumoniae strains. Proteins isolated according to the methods of this invention, when separated by SDS-PAGE, demonstrate some size variability (See FIG. 6) from about 90 kDa to about 110 kDa (±5 kDa). This variability can be attributed, at least in part, to the variability in length of the choline binding repeat region. The proteins of this invention also include a series of peptides at the carboxy terminus of the choline binding repeat region.

FIG. 1 provides a comparison of the amino acid sequence from a region containing the choline binding repeat region from PbcA for three different S. pneumoniae strains: CP1200, R6x and 23F(BD23). The amino acids in the boxes represent variations in the 23F (virulent strain BD23) choline binding domain repeat region (SEQ ID NOS:9, 10, and 11).

One example of a fragment containing nucleic acid encoding PbcA protein is provided in SEQ ID NO:4. The nucleic acid sequence encoding PbcA in strain CP1200 is provided as SEQ ID NO:5 (see Table 2). In another aspect of this invention, a protein of this invention has the amino acid sequence of SEQ ID NO:6. In one embodiment, a protein of this invention includes amino acids 1–410 of SEQ ID NO:6. In addition, variability between strains has been identified at the amino acid and nucleic acid level. For example, the amino terminus contains some variability and SEQ ID NO:1 may lack the first threonine residue. In general, PbcA proteins include C3 binding proteins from S. pneumoniae that preferably have at least 80% nucleic acid homology within the DNA of the amino terminus-containing region (the region amino-terminal to the choline binding repeats) to SEQ ID NO:5. More preferably, the PbcA proteins have at least 95% homology to the amino terninus-containing region of PbcA and still more preferably the PbcA protein includes SEQ ID NO:1. In another embodiment the PbcA proteins additionally include SEQ ID NO:2 or SEQ ID NO:3.

In one example, the nucleic acid encoding PbcA can be obtained from a variety of S. pneumoniae strains. A S. pneumoniae genomic library can be prepared using S. pneumoniae genomic DNA and in a preferred example, an S. pneumoniae genomic library was prepared using the CP1200 strain. Custom libraries can be obtained using a variety of standard methods for library construction. in these studies genomic DNA from S. pneumoniae was given to a commercial custom library supplier (Stratagene. LaJolla, Calif.). In one example, S. pneumoniae CP1200 strain genomic DNA was used to prepare the library (Example 5) The results of these studies identified a cloned nucleic acid fragment encoding PbcA. This fragment is useful for identifying PbcA encoding nucleic acid in other S. pneumoniae strains and the nucleic acid can be incorporated into vectors including expression vectors, for example to produce recombinant protein using methods such as those described by Sambrook et al. (cited below).

PbcA is preferably encoded by nucleic acid that is capable of hybridizing to at least 500 bp from the amino terminus region of SEQ ID NO:5 under hybridization conditions of about 6×SSC, 5×Denhardt's, 0.5% SDS, 100 μg/ml denatured, fragmented salmon sperm DNA hybridized overnight at 65° C. and washed in 2×SSC, 0.1% SDS, one time at room temperature for about 10 mn, followed by one time at 65° C. for about 15 mn and followed by at least one wash in 0.2×SSC, 0.1% SDS at room temperature for about 3–5 minutes. The protein of this invention preferably includes at least two and preferably at least three choline binding repeats.

This invention also relates to nucleic acid fragments of at least 20 bp from SEQ ID NO:5 and to isolated nucleic acid fragments of at least 100 base pairs that hybridize to the S. pneumoniae genome or to SEQ ID NO:5 under the hybridization conditions of about 6×SSC, 5×Denhardt's, 0.5% SDS, 100 μg/ml denatured, fragment salmon sperm DNA hybridized overnight at 65° C. and washed in 2×SSC, 0.1% SDS, one time at room temperature for about 10 min., followed by one wash at 65° C. for about 15 min and followed by at least one wash in 0.2×SSC, 0.1% SDS at room temperature for about 3–5 minutes. Preferably the nucleic acid fragments of at least 100 base pairs are part of a nucleic acid sequence that encodes a C3 binding protein that is at about 90 kDa to about 110 kDa. Preferably the nucleic acid fragment encodes a protein having at least two choline binding repeats.

As demonstrated in Example 3, the immunogenicity of PbcA can be studied by testing for the presence of antibodies to PbcA in acute and convalescent sera from patients with culture-proven pneumococcal infection. S. pneumoniae proteins can be separated by SDS-PAGE electrophoresis, transferred to nitrocellulose, and incubated with acute or convalescent serum (standard Western blot procedure). Results to detect the presence of antibodies to PbcA in human sera indicated that acute serum did not contain antibodies to any pneumococcal proteins released into the supernatant but that convalescent serum contained antibodies that recognized a band on an acrylamide gel with a molecular weight of PbcA.

PbcA, or fragments of PbcA, can be used to produce antibodies specific to PbcA. The termr "specific" is used to mean that when the antibodies to PbcA or fragments thereof are used in Western blots containing PbcA or a PbcA fragment or peptide under standard Western Blot assay conditions, the antibodies recognize only PbcA or its degradation or truncated products. Purified PbcA or fragments, preferably of at least about 15 amino acids in length, can be used to inject laboratory aniimals for the production of polyclonal and monoclonal antibodies to PbcA. Those skilled in the art will recognize that the methods for producing polyclonal antibodies and for producing monoclonal antibodies are known in the art and include the methods disclosed by Harlow et al. (cited below). Purified antibodies can be generated using the isolated protein of this invention, or fragments thereof, without undue experimentation. The antibodies are useful in in vitro assays to test for the presence or absence of PbcA protein and to test for the ability of the antibodies to block C3 binding as well as in in vivo assays to test for the ability of the antibodies to provide passive protection against pneumococcal infection, whether local or systemic. Antibody fragments and chimeric antibodies can be used and the antibodies include at least one variable domain from an antibody specifically recognizing PbcA.

Moreover, purified proteins, peptides and polypeptides from PbcA can be injected into animals, and later hunans, to produce an antibody response to *S. pneumoniae*. As used herein, the terms proteins, peptides and polypeptides are used interchangeably. Therefore, for purposes of this application and as used in the claims, a protein refers to proteins, protein fragments, peptides and polypeptides. Methods for introducing the protein, peptide or polypeptide fragment of PbcA to a mammal with an appropriate adjuvant, if necessary, are known in the art. Moreover, all or a portion of PbcA can be produced as an isolated protein or as a recombinant protein. Recombinant proteins can include all or a part of PcbA or can be formed as a chimeric protein. As used herein, the term "chimeric protein" refers to a recombinant protein including all or at least 15 amino acids of PcbA and amino acid sequence from at least one other protein positioned amino to, carboxy to, or on either side of the PbcA-derived amino acid. The 15 amino acids of PbcA of the chimeric protein are preferably unique to *S. pneumoniae*-derived proteins. Since patients with cleared *S. pneumoniae* infection have convalescent antibodies recognizing PbcA, it is known that the immune system can mount an immune response that includes the production of antibodies to PbcA. Ultimately, PbcA can be used as an immunogen for a pneumococcal vaccine. Further, based on the findings of these studies, antibody produced from the isolated protein, PbcA. can be used in Western Blot analyses to determine whether or not a particular *S. pneumoniae* strain's virulence or avirulence has been associated with the presence or absence of PbcA.

As demonstrated in Example 4, PbcA is implicated in pneunococcal virulence (see Example 4). In this example an avirulent 23F pneumococcal isolate was inoculated into the ears of chinchillas. Virulent pneumococcal isolates typically cause otitis media and the influx of leukocytes after injection at concentrations as low as $1 \times 10^2$ colony forming units (cfu). In contrast, the avirulent 23F strain was inoculated at concentrations of up to about $1 \times 10^7$ cells and even at that level was unable to cause otitis media or inflammation (Giebink et al. *J. Infect. Dis.* 1993, 167:347–355). As discussed in Example 4, studies disclosed here indicate that the avirulent strain reported by Giebink lacked detectable PbcA protein by Western blot. To further study the implications of PbcA on virulence, an insertion/duplication mutation of PbcA was prepared for further study (see Example 8).

The present invention provides a detailed method of purification of PbcA and studies indicat that PbcA is: (a) immunogenic in man; (b) conserved within the mass range of about 90 kDa to about 110 kDa (as observed on a 15% SDS-PAGE gel) among a variety of pneumococcal serotypes (that is, PbcA has been identified in a variety of serotypes); and (c) absent in an avirulent 23F strain that is incapable of causing otitis media in a chinchilla model.

To demonstrate that PbcA can be detected in an ELISA assay, PbcA coated wells of an ELISA plate were incubated with antibody prepared to purified PbcA from *S. pneumoniae* strain CP1200.

To demonstrate the ability of PbcA to bind human C3, purified PbcA from CP1200 was used to coat ELISA plates and the coated protein was incubated with methylamine-treated human C3. The binding of methylamine-treated human C3 was assessed using antibody to human C3 conjugated with horeseradish peroxidase (See Example 7). FIG. 2 is a graph illustrating the ability of PbcA to bind increasing concentrations of human C3. Specific antibody to PbcA blocked thebinding of purified human C3 to PbcA in a dose-dependent fashion. These experiments are detailed in Example 7 and in FIG. 3. The Western blot (FIG. 3*a*) demonstrates that the IgG fraction of antibody to PbcA blocked the binding of human C3 to PbcA immobilized on nitrocellulose. The graph (FIG. 3*b*) demonstrates that affinity-purified antibody to PbcA blocked the binding of human C3 to PbcA immobilized on ELISA plates.

Figure 4:
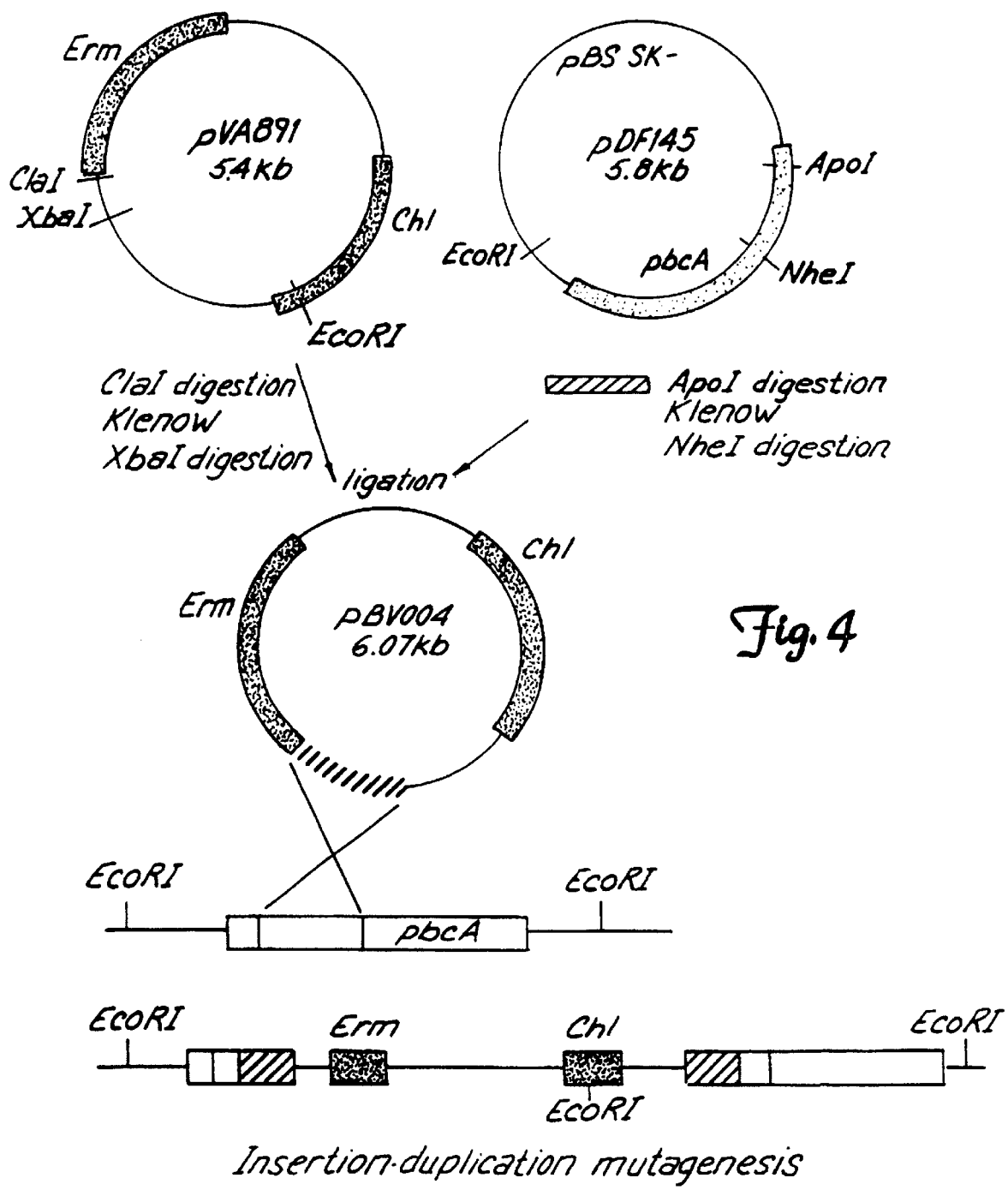

A PbcA insertion construct was prepared to interrupt a pbcA gene in CP1200 and R6x. An exemplary protocol is provided in Example 8 for producing an exemplary construct suitable for homologous recombination. FIG. 4 illustrates a preferred method for preparing an insertion construct to inactivate the pbcA gene in *S. pneumoniae*. In these methods, a gene encoding PbcA (a non-native C3 binding protein) is introduced into a cell containing PbcA. The non-native C3 binding protein is homologous to the PbcA in the cell to facilitate homologous recombination and the production of insertional mutations. The presence of the insertion mutant was confirmed by Southern blot for a number of mutated R6x and CP1200 strains following transformation of these strains with the mutating construct pBV004 (see FIG. 4). Mutated strains were tested by Southern blot using a 1.5 kb fragment of pbcA or vector pVA891 probes. Wild type strain BD23 was not transformed in these studies. Results of the Southern blot experiments are provided in FIG. 5.

The insertion mutants were tested for their ability to produce PbcA protein using either human C3 or antibody to PbcA (FIG. 4). Results indicated that no protein approximating the size of PbcA was detectable in supernatants from the *S. pneumoniae* strains tested on Western blot. Further, neither C3 nor antibody to PbcA bound on the Western blots. Therefore, the mutants are useful to assess functional aspects of PbcA and to serve as a negative control for a variety of PbcA-related experiments.

As noted above, PbcA binds noncovalently to C3. *S. pneumoniae* is generally cleared from the body by the covalent opsonic deposition of C3b on the pneumococcal capsule or cell wall, followed by phagocytosis via C3 receptors or Fc receptors on neutrophils or monocytes/macrophages. Nonopsonic (i.e. non-covalent) binding of C3 by pneumococcal surface proteins, such as PbcA, suggests a mechanism whereby pneumococci can evade opsonization. Without intending to limit the scope of this invention, it is possible that PbcA protein from *S. pneumoniae* could bind C3 in vivo and reduce the amount of C3 available for opsonization. Antibodies to PbcA could block the C3-binding effect and restore the opsonic activity of C3 in plasma.

PbcA can be used in in vitro assays to assess the effect of PbcA on cells. For example, in Example 6, purified PbcA was added to cell cultures to study the role of PbcA in *S. pneumoniae* pathogenesis. PbcAcan be tested for its toxicity on a variety of cells as well as tested in in vivo models for toxicity. The results of Example 6 indicated that PbcA, as an intact protein, was toxic to pulmonary epithelial cells and that it stimulated production of the cytokine IL-8 from the epithelial cells. IL-8 is a cytokine that, among other things, stimulates neutrophil migration. Increased concentrations of neutrophils are observed in the lungs of patients with significant *S. pneumoniae* infection in the lung passageways. Neutrophils and other white blood cells produce a variety of degradatory enzymes that damage lung tissue in *S. pneumoniae* infection and, based on these studies, lung damage can be the result of enzymatic release from white blood cells, PbcA. or both.

*S. pneumoniae* can colonize the nasopharynx, infect the lung and ultimately disseminate to the blood, meninges or other sites. Antibody to PbcA can be tested for its ability to reduce the toxicity of the organism to the lung tissue and antibody to PbcA can be tested for its ability to prevent PbcA binding to C3 and to permit C3 to remain available during *S. pneumoniae* infection. Similarly, peptides and polypeptides to PbcA can be administered to mammals and used in studies to assess the ability of the immune system to produce antibody to limit *S. pneumoniae* infection.

Animal models to study *S. pneumoniae* pathogenesis are known in the art. These include, but are not limited to, the chinchilla model for otitis media, the infant rat model for *S. pneumoniae* colonization and bacteremia, the mouse model for colonization, bacteremia and meningeal infection and a rabbit model for studying infection in the meninges. Those of ordinary skill in the art will recognize that antibodies to PbcA (whether exogenously administered or the product of inmmunization with all or a part of PbcA) can be tested in these models for their ability to limit or inhibit *S. pneumoniae* infection. Exogenously (i.e., passively) administered antibody can be given through a variety of parenteral routes including, but not limited to, intravenous administration or administration to the air passages of a mammal such as a mouse, chinchilla, rat, rabbit or human.

All references and publications cited herein are expressly incorporated by reference into this disclosure. Particular embodiments of this invention will be discussed in detail and reference has been made to possible variations within the scope of this invention. There are a variety of alternative techniques and procedures available to those of skill in the art which would similarly permit one to successfully perform the intended invention.

EXAMPLE 1

Identification of PbcA from *S. pneumoniae*

10 ml of *S. pneumoniae* strain CP1200 (obtained from D. A. Morrison. University of Illinois, Champagne-Urbana, Ill. and described in Havarstein L. F., et al. *Proc. Natl. Acad. Sci.* (*USA*) 1995;92:1 1140–11144) was grown to exponential phase (O.D.$_{620}$=0.3) in Todd Hewitt broth (Fisher, Pittsburgh, Pa.) or in a synthetic medium (O.D.$_{620}$=0.15, media described by Sicard, A. M. *Genetics* 1964 59:31–44). Pneumococcal cells were pelleted and the supernatant was removed and precipitated with a final concentration of 10% trichloroacetic acid (TCA) at 4° C. overnight and samples were electrophoresed on 15% sodium dodecyl sulfate polyacrylamide gels (SDS-PAGE) under non-reducing conditions. Pneumococcal proteins separated by electrophoresis were then transferred to nitrocellulose for Western blotting. After blocking of the Western blot according to standard protocols (Harlow, et al. *Antibodies; A Laboratory manual.* Cold Spring Harbor, N.Y.; Cold Spring harbor Laboratory Press, 1988; 471–5 10) the blot was incubated with 10 mls of binding buffer containing about 2 μg/ml of purified human C3 (Hostetter et al. *J. Infect. Dis.* 994; 150:653–661), labeled with biotin. The blot was washed and incubated ith a 1:20,000 dilution of HRP-avidin for 60 minutes at room temperature and eveloped using the Supersignal™ system (Pierce, Rockford, Ill.) according to manufacturer's instructions. Purified human C3 bound to a band of about 90 kDa under non-reducing and reducing conditions on a 15% SDS-PAGE gel. Similarly, a protein of about 90 kDa was detected when cells were lysed in 5% SDS at room temperature for 30 minutes and following centrifugation, the supernatant was separated on a 15% SDS-PAGE gel.

Experiments were repeated with the substitution of 2 μg/ml biotinvlated C3 after treatment with methylamine (using the methods disclosed a in Hostetter. et al. *J. Infect. Dis.* 1984; 150:653–661) to demonstrate that the 90 kDa protein in pneumococcal supernatants and lysates could bind non-opsonic forms of C3. Results again indicated that a 90 kDa protein was recognized by C3. A variety of pneumococcal strains were also tested. C3 bound to PbcA identified in Western blots using supernatants from a variety of virulent pneumococcal strains (serotypes 1,3 [4 strains], 4, 14, 19F)

EXAMPLE 2

Purification of PbcA

*S. pneumoniae* CP1200 was grown to mid-exponential phase in 4 liters of Todd Hewitt broth at 37° C. Pneumococcal cells were pelleted by centrifugation at 10,000×g for 10 minutes. Proteins in the supematant were precipitated with a final concentration of 10% trichloroacetic acid at 4° C. overnight. The precipitate was resuspended in 40 mls of 100 mM Tris and the final pH adjusted to 7.0. The resuspended proteins were chromatographed on a 1.2 ml column of Thiopropyl Separaose 6B coupled by a disulfide bond to 4 mg methylamine treated human C3. The column was then washed with 40 ml of 100 mM Tris-HCl, pH 7.0 containing 0.5 M NaCl. PbcA was eluted from the column with 20% ethanol in the Tris-HCl/NaCl wash buffer. 1 ml. fractions were collected and analyzed by SDS-PAGE and C3 binding assay. A protein of about 90 kDa to about 110 kDa (+/−5 kDa) eluted from the C3 affinity column in fractions 2–10.

Multiple eluates from sequential purifications of PbcA from strain 1200 were pooled by precipitation with 90% ethanol to obtain sufficient sample for sequencing and further protein studies. Approximately 80 picomoles of the protein were subjected to amino terminal analysis and tryptic digestion for internal peptide sequencing at the Harvard Microchemical Facility (Cambridge, Mass.).

EXAMPLE 3

Immunogenicity of PbcA

Immunogenicity of PbcA was assessed by growing 10 ml of *S. pneumoniae* strain CP1200 to exponential phase in Todd Hewitt broth, pelleting the cells, and precipitating proteins from the supernatant with 10% TCA overnight at 4° C. The next day, supernatant proteins were electrophoresed on 15% SDS-PAGE, transferred to nitrocellulose, blocked with skim milk in a standard protocol (Harlow, et al. supra) and incubated with a 1:10,000 dilution of acute or convalescent serum from a patient infected with *S. pneumoniae* (Dr. E. Janoff, Minneapolis Va. Hospital, Minneapolis, Minn.). The blot was washed according to methods disclosed in Harlow et al. and incubated with a 1:50,000 dilution of commercially purchased goat anti-human IgG conjugated to horseradish peroxidase (Chemicon, Temicula, Calif.). The blot was-washed and developed with the Supersignal™ system according to manufacturer's instructions.

Western blots from these studies demonstrated that acute serum did not contain IgG antibodies to any pneumococcal proteins released into the supernatant but that convalescent serum contained IgG antibodies that recognized a protein of 90 kDa, consistent with the mass of PbcA. These experiments confirmed that PbcA elicited an immune response in humans recovering from S. pneumoniae infection and indicated that PbcA is recognized by the human immune system.

EXAMPLE 4

PbcA is Implicated in S. pneumoniae Virulence

Virulent pneumococcal isolates typically cause otitis media and influx of leukocytes after inoculation in concentrations as low as $1 \times 10^2$ (Giebink et al. *J. Infect. Dis.* 1993; 167:347–355). Giebink et al. reported that an avirulent serotype, type 23F, was inoculated into the ears of chinchillas and that inoculum at concentrations of less than about $1 \times 10^7$ cells was unable to cause otitis media or inflammation.

Both the type 23F avirulent strain (GD 23, supra) and a type 23F virulent strain (BD23, Dr. Steve Pelton, Boston City Hospital, Boston, Mass.) were grown to mid-exponential phase in Todd Hewitt broth, the cells were pelleted, and supernatant proteins were precipitated in a final TCA concentration of 10% overnight at 4° C. The following day, the precipitate was resuspended in about 1 ml Tris, neutralized to pH 7.0, electrophoresed on 15% SDS-PAGE and then transferred to nitrocellulose. Incubation of the nitrocellulose membrane with 2 μg/ml of biotinylated, methylamine-treated C3 in binding buffer and development of the Western blot with avidin conjugated to horseradish peroxidase detected a PbcA band from a 15% SDS-PAGE gel in both cell lysates and supematants from the virulent type 23F, but PbcA was completely absent in cell lysates and supernatants from the avirulent type 23F. In place of PbcA. a smaller band of 33 kDa was identified. This band may represent adegradation product or a truncated version of PbcA.

EXAMPLE 5

Isolation of Nucleic Acid Encoding PbcA

Degenerate oligonucleotides were obtained from a commercial supplier based on the sequence of SEQ ID NO:1 and SEQ ID NO:2. The oligonucleotides were used to amplify a 1500 bp sequence from CP1200 genomic DNA as template using standard polymerase chain reaction technology. Template, primers, and buffer were added for one 5-minute cycle at 94° C. Then dNTP's and Taq polymerase were added for 30 cycles, as follows: Double stranded DNA was denatured for 1 min at 94° C., annealed for 1 min at 50° C., and extended for 2 min at 72° C. Final extension was completed in one 8-minute cycle at 72° C. The 1500 bp sequence was random primer labeled using a commercial kit and the sequence was used to screen the CP1200 genomic DNA library prepared under our direction by Stratagene (LaJolla, Calif.). Hybridization was performed under at least moderate stringency conditions and a variety of hybridization methods are provided in Sambrook et al. (*Molecular Cloning, A Laboratory Manual*, 1989 Cold Spring Harbor Laboratory Press, Cold Spring Harbor, N.Y.). Exemplary hybridization conditions used were 65° C. hybridization in 6×SSC (1M NaCl) using 5×Denhardt's, 20 mM sodium phosphate, 0.5% SDS and 100 μg/ml denatured sonicated salmon sperm DNA.

Three clones were identified that hybridized to the 1500 bp genomic DNA fragment; two overlapping clones of 4.3 and 5.3 kb, respectively and a third clone of 2.5 kb. Restriction mapping and hybridization studies suggested that the 5.3 kb clone contained an open reading frame encompassing the oligonucleotides from SEQ ID NO:1 and SEQ ID NO:2. A 3.2 kb fragment remaining after HindIII digestion and religation of the 5.3 kb clone is sequenced.

EXAMPLE 6

Stimulation of IL-8 Production from Pulmonary Epithelial Cells in Response to PbcA Monolayers of type II pulmonary epithelial cells (A549, American Type Culture Collection (ATCC), Rockville, Md.) were incubated for 4 hours in culture supernatant (at least about 15 μl supernatant diluted in 1 ml. serum free media (50% Hams F12/50% PBS) from exponentially growing S. pneumoniae (Pn) laboratory strain (CP1200, supra) or clinical isolates grown in Todd Hewitt broth (supra). Incubation of the epithelial cell monolayer in the culture supernatant induced the release of about 1169 pg/ml IL-8 while incubation in media alone without culture supernatant and incubation in pneumococcal growth medium alone without culture supernatant was significantly less (p<0.0001, see table below).

Supernatants from a virulent S. pneumoniae clinical isolate, 23F, were also effective at stimulating IL-8 production from pulmonary epithelial cells (about 1,495 pg/ml IL-8). Supernatants from a 23F strain that did not produce otitis media in an animal model did. not induce IL-8 release in vitro.

Increasing the time for which CP 1200 supernatants were incubated with the epithelial monolayer from 4 to 24 hours resulted in an increase in IL-8 production to approximately two times the level of IL-8 obtained after a 4 hour incubation.

SDS-PAGE analysis of proteins in CP 1200 S. pneumoniae supernatants indicated that there a variety of proteins in the supernatants including five discrete bands correlating to identifiable proteins from S. pneumoniae that had sizes of about 180 kDa, 90 kDa, 57 kDa 42 kDa and 24 kDa. All five proteins were present in supernatants from the virulent 23F strain during exponential growth, but a band of about 90 kDa to about 110 kDa was absent in supernatants from the avirulent 23F strain.

In identical assays, about 150–200 ng of affinity purified PbcA protein elicited at least about 1200 pg/ml IL-8 from pulmonary epithelial cells. This level was similar to that elicited using supernatants from CP1200 and virulent 23F strains after a 4-hour incubation. Thus, not only is PbcA potent in eliciting IL-8 from pulmonary epithelial cells.

The combined results from 11 separate assays for IL-8 production are provided below:

| Stimulus | IL-8 Release (pg/ml) mean ± S.E. |
| --- | --- |
| Medium alone | 580 ± 40 |
| Pneumo supt. Avir 23F(GD23) | 471 ± 72 |
| Pneumo supt. Vir23F(BD23) | 1,138 ± 83 |
| Pneumo supt. CP1200 | 1,169 ± 121 |
| 200 ng PbcA(CP1200) | 1,679 ± 113 |
| 150 ng PbcA(CP1200)* | 1,201 |

*assayed once

Rabbit polyclonal antibody prepared against PbcA was used to determine whether the toxicity and IL-8 production stimulated by PbcA was inhibited by PbcA-specific antibody as confirmation that the effects observed in these studies were attributable to PbcA.

EXAMPLE 7

PbcA Binds Human C3

C3/PbcA ELISA Binding Assay

Purified PbcA was bound to ELISA 8-well strips (Costar, Cambridge, Mass.) overnight in binding buffer at room temp at varying concentrations (0.5 µg/well and 0 µg/well). Wells were blocked with 5% Milk, 0.05% Tween 20 in PBS and 0.02% azide for 2 hours, washed 3 times with 0.05% Tween 20 in PBS and C3 was added (5 µg/well) in antibody diluent buffer (1% BSA, 1% Tween 20 in PBS) for 2 hours at 37° C. Plates were washed 3 times and incubated with HRP-conjugated goat anti-human C3 (1 µg/ml) for 1 hour at 37° C. Plates were washed 3 times, developed with OPD (Zymed protocol) for 30 minutes, and the absorbence was read at $A_{490}$ on an ELISA plate reader.

A standard curve was prepared to assess saturation of PbcA on the plate. Serial dilutions of PbcA protein were added (from 500 ng/well to 0 ng/well) to microtiter wells. Plates were incubated for 1 hour at 37° C. with anti-PbcA (1:100), washed, incubated with HRP-conjugated goat anti rabbit (1:2000) for 1 hour at 37° C. Plates were washed and developed with a 1:10 dilution of OPD developing buffer for 20 minutes at room temperature as per manufacturer's instructions and read at $A_{490}$ on an ELISA plate reader.

Binding of C3 was determined by the immobilization of 500 ng PbcA/well. C3 was added in serial dilutions from 10 µg/well to 0 µg/well and incubated with immobilized PbcA for 2 hours at 37° C. Goat HRP-conjugated anti-human C3 (1 µg/well) was added and the absorbance was assessed. FIG. 2 shows a dose-response curve for the binding of increasing amounts of C3 to constant amounts of inmobilized PbcA.

Results indicated (see FIG. 2) that increasing concentrations of C3 bound to 0.5 µg/well PbcA on the plate and saturated with a plateau of 6 µg/well.

Initial blocking experiments were done using the IgG fraction of anti-PbcA polyclonal antibodies (2 to 8-fold molar excess over 500 mg PbcA added per well). The IgG fraction of serum from unimmunized rabbits served as a control. After PbcA protein was bound to the plate overnight and blocked for 2 hours, anti-PbcA antibodies were added for 1 hour at 37° C. prior to the addition of C3. Plates were washed, 6 µg C3 was added to each well for 2 hours at 37° C. Plates were then incubated with goat HRP-conjugated anti-human C3 for 1 hour at 37° C. then washed and developed for 4 minutes.

Both the IgG fraction of anti-PbcA antibodies and affinity purified antibodies inhibited C3 binding up to 50% while control IgG antibodies did not inhibit C3 binding. FIG. 3a (Western blot) demonstrates that the IgG fraction of anti-PbcA blocked the binding of human C3 to PbcA immobilized on nitrocellulose. FIG. 3b demonstrates that affinity-purified anti-PbcA blocked the binding of C3 to PbcA by 40–50%, while those antibodies remaining in rabbit serum after the removal of anti-PbcA antibodies had no blocking effect.

EXAMPLE 8

Production of pbcA Insertion/Duplication Mutants of *S. Pneumoniae*

Generation of a pbcA Insertion/Duplication Construct

To generate an insertion/duplication mutant ofpbcA, a 761 bp fragment was isolated from pDF145 (a plasmid containing pbcA) first by digestion with ApoI (New England Biolabs) followed by the addition of DNA Polymerase I, Large (Klenow) Fragment to create a blunt end, and second by digestion with NheI to create a 5' overhang sticky end compatible with XbaI in the vector pVA891. This vector is a streptococcal/*E. coli* shuttle vector that replicated in *E. coli* but not in *S. pneumoniae* (from Dr. Gary Dunny, Dept. Microbiology, University of Minnesota, Minneapolis, Minn. and described in Macrina FL, et al. *Gene* 25:145–150, 1983). The 761 bp fragment was isolated on a 0.7% agarose gel. Concurrently, the vector pVA891 was digested with ClaI and treated with Klenow to create a blunt end, followed by digestion with XbaI to create a 5' sticky end. The 761 bp fragment of pbcA was ligated into the pneumococcal vector pVA891 and transformed into competent DH5αE. coli. Tranformants were selected by resistance to chloramphenicol and plasmid DNA from 12 clones was cut with EcoRI and SpeI (the 761 fragment introduced a SpeI site). This confirmed the presence of the insert DNA in clones 2–12 and the absence of the insert in the control vector clone. Clone 4 was selected as construct pBV004 and DNA was transformed into unencapsulated laboratory strains R6x and CP1200 and selected by erythromycin (Erm) resistance.

Transformation of Knockout Construct for Insertion/Duplication Mutagenesis

Pneumococcal strains CP1200 and R6x were grown to $OD_{550}$=0.2 and stored as frozen stock aliquots. Pneumococcal cultures were diluted 1:100 to 0.002 and grown to $OD_{550}$=0.02. Competence was induced by the Morrison CSP protocol (Haverstein, L. et al. *Proc. Natl. Acad. Sci. (USA)* 92:11140–11144, 1995). To 100 µl of cells, competence stimulating peptide (CSP) 100 ng, was added along with 500 ng to about 1 µg of construct pBV004 DNA. Cells were incubated for 30–40 minutes in a 37° C. water bath with aeration to maintain constant temperature. After transformation, cells were diluted 1:10 in one ml total volume of THB+Y. DNase I (10 µg/ml) was added and cells were incubated an additional 90 minutes to allow integration. The transformation mixture was diluted 1:10 and 100 µl of cells were plated in a 4-layer agar overlay procedure as follows: first overlay, 3 mls THB agar; second overlay, 1.5 mls THBY+1.5 mls THB agar+100 µl transformation mixture, incubate 1 hour at 37° C.; third overlay, 3 mls THB agar, fourth overlay, 3 mls THB agar+0.05 µg/ml Erythromycin.

Genomic DNA was isolated from wild type R6x, CP1200 and BD23(virulent 23F strain supra) strains as well as from insertional mutants in R6x and CP1200. Genomic DNA was digested with EcoRI (which does not cut within the pbcA gene) and electrophoresed in 0.7% agarose, blotted onto nylon membrane and Southern blot performed with digoxygenin-labeled probes.

Referring to FIG. 5, on the left are the results of a the Southern blot using the 1.5 kb fragment of pbcA as the probe. The probe hybridized with wild-type pneumococcal DNA in a single band and hybridized with two bands in the mutants R62r, R63r, R6x5 and CP1r, as expected.

On the right, the same blot was stripped and reprobed with pVA891 vector DNA. Wild-type DNA does not hybridize with pVA891, while the vector probe hybridizes at the same two bands indicating that the insertion mutagenesis was within the pbcA gene.

Figures 6A, 6B:
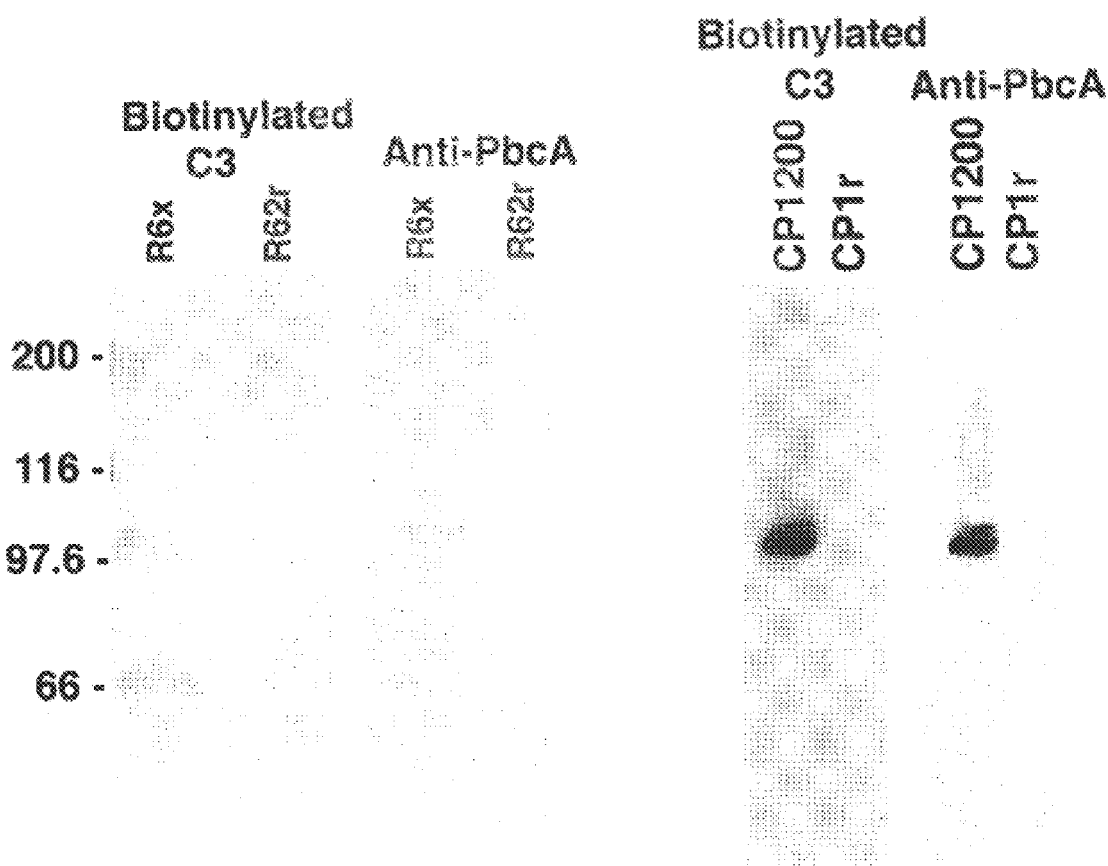

To confirm that the insertion mutated the gene and disrupted protein production, a Western blot analysis was performed (see FIG. 6).

On the left, trichloroacetic acid (TCA) precipitated supernatants from strain R6x and the R62r mutant were electrophoresed on a 7.5% SDS-PAGE gel and blotted with either anti-PbcA antibodies and HRP-goat- anti-rabbit antibodies for detection of PbcA or with biotinylated C3 and HRP-avidin for detection of C3 binding. Insertional mutants did not synthesize PbcA and failed to bind to anti-PbcA antibodies or biotinylated C3. Absence of protein and lack of C3 binding was seen in the mutant compared to wild-type. The PbcA protein from R6x is larger than that of CP 1200.

The original CP 1200 detected a 90 kDa protein and had a truncated choline binding region due to premature termination. The R6x PbcA protein was about 105 lkDa and appears to contain at least 9 choline binding repeats.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive scope of this application.

What is claimed is:

1. A method for isolating a C3 binding protein from a bacterium comprising the steps of:

obtaining a protein sample from a bacterium;

applying the sample to a solid support comprising methylamine treated complement protein C3;

washing the solid support; and removing a C3 binding protein from the solid support in a solution comprising alcohol;

wherein the C3 binding protein does not cleave or degrade C3.

2. The method of claim 1 wherein the bacterium is *S. pneumoniae*.

3. The method of claim 1 wherein the solid support comprises an affinity column.

4. The method of claim 1 wherein the alcohol is ethanol.

5. The method of claim 4 wherein the solution comprising alcohol is a buffer comprising 20% ethanol.

* * * * *

UNITED STATES PATENT AND TRADEMARK OFFICE
CERTIFICATE OF CORRECTION

PATENT NO. : 6,291,654 B1 Page 1 of 1
DATED : September 18, 2001
INVENTOR(S) : Hostetter et al.

It is certified that error appears in the above-identified patent and that said Letters Patent is hereby corrected as shown below:

<u>Column 1,</u>
Line 12, before the paragraph entitled "FIELD OF THE INVENTION", please insert the following paragraph:

-- STATEMENT OF GOVERNMENT RIGHTS

The present invention was made with government support under Grant No. R01-AI24162, awarded by the National Institutes of Health/National Institutes of Research Resources. The Government may have certain rights in this invention. --

Signed and Sealed this

Second Day of July, 2002

Attest:

Attesting Officer

JAMES E. ROGAN
*Director of the United States Patent and Trademark Office*

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 20 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Thr Glu Asn Glu Gly Ser Thr Gln Ala Ala Thr Ser Ser Asn Met Ala
1               5                   10                  15

Lys Thr Glu His
            20

(2) INFORMATION FOR SEQ ID NO:2:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Glu Lys Pro Ala Glu Gln Pro Gln Pro Ala Pro Ala Thr Gln Pro
1               5                   10                  15

(2) INFORMATION FOR SEQ ID NO:3:

(i) SEQUENCE CHARACTERISTICS:
      (A) LENGTH: 17 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:3:

Ser Ser Asp Ser Ser Val Gly Glu Glu Thr Leu Pro Ser Ser Ser Leu
1               5                   10                  15

Lys (2) INFORMATION FOR SEQ ID NO:4:

(i) SEQUENCE CHARACTERISTICS:
      (A) LENGTH: 3023 base pairs (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

```
GTAATACGAC TCACTATAGG GCGAATTGGG TACCGGGCCC CCCCTCGAGG TCGACGGTAT      60

CGATAAGCTT ATGCTTGTCA ATAATCACAA ATATGTAGAT CATATCTTGT TTAGGACAGT     120

AAAACATCCT AATTACTTTT TAAATATTCT TCCTGAGTTG ATTGGCTTGA CCTTGTTGAG     180

TCATGCTTAT GTGACTTTTG TTTTAGTTTT TCCAGTTTAT GCAGTTATTT TGTATCGACG     240

AATAGCTGAA GAGGAAAAGC TATTACATGA AGTTATAATC CCAAATGGAA GCATAAAGAG     300

ATAAATACAA AATTCGATTT ATATACAGTT CATATTGAAG TAATATAGTA AGGTTAAAGA     360

AAAAATATAG AAGGAAATAA ACATGTTTGC ATCAAAAAGC GAAAGAAAAG TACATTATTC     420

AATTCGTAAA TTTAGTATTG GAGTAGCTAG TGTAGCTGTT GCCAGTCTTG TTATGGGAAG     480

TGTGGTTCAT GCGACAGAGA ACGAGGGAAG TACCCAAGCA GCCACTTCTT CTAATATGGC     540

AAAGACAGAA CATAGGAAAG CTGCTAAACA AGTCGTCGAT GAATATATAG AAAAAATGTT     600

GAGGGAGATT CAACTAGATA GAAGAAAACA TACCCAAAAT GTCGCCTTAA ACATAAAGTT     660

GAGCGCAATT AAAACGAAGT ATTTGCGTGA ATTAAATGTT TTAGAAGAGA AGTCGAAAGA     720

TGAGTTGCCG TCAGAAATAA AAGCAAAGTT AGACGCAGCT TTTGAGAAGT TTAAAAAAGA     780

TACATTGAAA CCAGGAGAAA AGGTAGCAGA AGCTAAGAAG AAGGTTGAAG AAGCTAAGAA     840

AAAAGCCGAG GATCAAAAAG AAGAAGATCG TCGTAACTAC CCAACCAATA CTTACAAAAC     900

GCTTGAACTT GAAATTGCTG AGTTCGATGT GAAAGTTAAA GAAGCGGAGC TTGAACTAGT     960

AAAAGAGGAA GCTAAAGAAT CTCGAAACGA GGGCACAATT AAGCAAGCAA AGAGAAAGT    1020

TGAGAGTAAA AAAGCTGAGG CTACAAGGTT AGAAAACATC AAGACAGATC GTAAAAAAGC    1080

AGAAGAAGAA GCTAAACGAA AAGCAGATGC TAAGTTGAAG GAAGCTAATG TAGCGACTTC    1140

AGATCAAGGT AAACCAAAGG GGCGGGCAAA ACGAGGAGTT CCTGGAGAGC TAGCAACACC    1200

TGATAAAAAA GAAAATGATG CGAAGTCTTC AGATTCTAGC GTAGGTGAAG AAACTCTTCC    1260

AAGCTCATCC CTGAAATCAG GAAAAAAGGT AGCAGAAGCT GAGAAGAAGG TTGAAGAAGC    1320

TGAGAAAAAA GCCAAGGATC AAAAAGAAGA AGATCGCCGT AACTACCCAA CCAATACTTA    1380

CAAAACGCTT GACCTTGAAA TTGCTGAGTC CGATGTGAAA GTTAAAGAAG CGGAGCTTGA    1440

ACTAGTAAAA GAGGAAGCTA AGGAACCTCG AGACGAGGAA AAAATTAAGC AAGCAAAAGC    1500

GAAAGTTGAG AGTAAAAAAG CTGAGGCTAC AAGGTTAGAA AACATCAAGA CAGATCGTAA    1560

AAAAGCAGAA GAAGAAGCTA AACGAAAAGC AGCAGAAGAA GATAAAGTTA AGAAAAAACC    1620

AGCTGAACAA CCACAACCAG CGCCGGCTAC TCAACCAGAA AAACCAGCTC AAAACCAGA    1680

GAAGCCAGCT GAACAACCAA AGCAGAAAA AACAGATGAT CAACAAGCTG AAGAAGACTA    1740

TGCTCGTAGA TCAGAAGAAG AATATAATCG CTTGACTCAA CAGCAACCGC CAAAAACTGA    1800

AAAACCAGCA CAACCATCTA CTCCAAAAAC AGGCTGGAAA CAAGAAAACG GTATGTGGTA    1860

CTTCTACAAT ACTGATGGTT CAATGGCAAC AGGATGGCTC CAAAACAACG GTTCATGGTA    1920

CTATCTAAAC GCTAATGGTG CTATGGCGAC AGGATGGCTC CAAAACAATG GTTCATGGTA    1980

CTATCTAAAC GCTAATGGTT CAATGGCAAC AGGATGGCTC CAAAACAATG GTTCATGGTA    2040

CTACCTAAAC GCTAATGGTG CTATGGCGAC AGGATAGCTC CAATACAATG GTTCATGGTA    2100

CTACCTAAAC AGCAATGGCG CTATGGCGAC AGGATGGCTC CAATACAATG GCTCATGGTA    2160
```

```
CTACCTCAAC GCTAATGGTG ATATGGCGAC AGGATGGCTC CAAAACAACG GTTCATGGTA      2220

CTACCTCAAC GCTAATGGTG ATATGGCGAC AGGATGGCTC CAATACAACG GTTCATGGTA      2280

TTACCTCAAC GCTAATGGTG ATATGGCGAC AGGTTGGGTG AAAGATGGAG ATACCTGGTA      2340

CTATCTTGAA GCATCAGGTG CTATGAAAGC AAGCCAATGG TTCAAAGTAT CAGATAAATG      2400

GTACTATGTC AATGGCTCAG GTGCCCTTGC AGTCAACACA ACTGTAGATG GCTATGGAGT      2460

CAATGCCAAT GGTGAATGGG TAAACTAAAC CTAATATAAC TAGTTAATAC TGACTTCCTG      2520

TAAGAACTTT TTAAAGTATT CCCTACAAAT ACCATATCCT TTCAGTAGAT AATATACCCT      2580

TGTAGGAAGT TTAGATTAAA AAATAACTCT GTAATCTCTA GCCGGATTTA TAGCGCTAGA      2640

GACTACGAG TTTTTTTGAT GAGGAAAGAA TGGCGGCATT CAAGAGACTC TTTAAGAGAG      2700

TTACGGGTTT TAAACTATTA AGCCTTCTCC AATTGCAAGA GGGCTTCAAT CTCTGCTAGG      2760

GTGCTAGCTT GCGAAATGGC TCCACGGAGT TTGGCAGCGC CAGATGTTCC ACGGAGATAG      2820

TGAGGAGCGA GGCCGCGGAA TTCACGAACT GCGACGTTTT CTCCTTTGAG GTTAATCAAT      2880

CGTTTCAGGA ATTCCGGAAT TCCGGAATTC CGGAATTCCG GAATTCCGGA ATTCCTGCAG      2940

CCCGGGGGAT CCACTAGTTC TAGAGCGGCC GCCACCGCGG TGGAGCTCCA GCTTTTGTTC      3000

CCTTTAGTGA GGGTTAATTT CGA                                            3023

(2) INFORMATION FOR SEQ ID NO:5:

(i) SEQUENCE CHARACTERISTICS:
        (A) LENGTH: 1695 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

CGAAACGAGG GCACAATTAA GCAAGCAAAA GAGAAAGTTG AGAGTAAAAA AGCTGAGGCT       60

ACAAGGTTAG AAAACATCAA GACAGATCGT AAAAAAGCAG AAGAAGAAGC TAAACGAAAA      120

GCAGATGCTA AGTTGAAGGA AGCTAATGTA GCGACTTCAG ATCAAGGTAA ACCAAAGGGG      180

CGGGCAAAAC GAGGAGTTCC TGGAGAGCTA GCAACACCTG ATAAAAAAGA AAATGATGCG      240

AAGTCTTCAG ATTCTAGCGT AGGTGAAGAA ACTCTTCCAA GCTCATCCCT GAAATCAGGA      300

AAAAAGGTAG CAGAAGCTGA GAAGAAGGTT GAAGAAGCTG AGAAAAAAGC CAAGGATCAA      360

AAAGAAGAAG ATCGCCGTAA CTACCCAACC AATACTTACA AAACGCTTGA CCTTGAAATT      420

GCTGAGTCCG ATGTGAAAGT TAAAGAAGCG GAGCTTGAAC TAGTAAAAGA GGAAGCTAAG      480

GAACCTCGAG ACGAGGAAAA AATTAAGCAA GCAAAAGCGA AGTTGAGAG TAAAAAAGCT       540

GAGGCTACAA GGTTAGAAAA CATCAAGACA GATCGTAAAA AAGCAGAAGA AGAAGCTAAA      600

ATGTTTGCAT CAAAAAGCGA AGAAAAGTA CATTATTCAA TTCGTAAATT TAGTATTGGA       660

GTAGCTAGTG TAGCTGTTGC CAGTCTTGTT ATGGGAAGTG TGGTTCATGC GACAGAGAAC      720

GAGGGAAGTA CCCAAGCAGC CACTTCTTCT AATATGGCAA AGACAGAACA TAGGAAAGCT      780

GCTAAACAAG TCGTCGATGA ATATATAGAA AAAATGTTGA GGGAGATTCA ACTAGATAGA      840

AGAAAACATA CCCAAAATGT CGCCTTAAAC ATAAAGTTGA GCGCAATTAA AACGAAGTAT      900

TTGCGTGAAT TAAATGTTTT AGAAGAGAAG TCGAAAGATG AGTTGCCGTC AGAAATAAAA      960

GCAAAGTTAG ACGCAGCTTT TGAGAAGTTT AAAAAAGATA CATTGAAACC AGGAGAAAAG     1020

GTAGCAGAAG CTAAGAAGAA GGTTGAAGAA GCTAAGAAAA AAGCCGAGGA TCAAAAAGAA     1080
```

```
GAAGATCGTC GTAACTACCC AACCAATACT TACAAAACGC TTGAACTTGA AATTGCTGAG     1140

TTCGATGTGA AAGTTAAAGA AGCGGAGCTT GAACTAGTAA AAGAGGAAGC TAAAGAATCT     1200

CGAAAAGCAG CAGAAGAAGA TAAAGTTAAA GAAAAACCAG CTGAACAACC ACAACCAGCG     1260

CCGGCTACTC AACCAGAAAA ACCAGCTCCA AAACCAGAGA AGCCAGCTGA CAACCAAAA      1320

GCAGAAAAAA CAGATGATCA ACAAGCTGAA GAAGACTATG CTCGTAGATC AGAAGAAGAA     1380

TATAATCGCT TGACTCAACA GCAACCGCCA AAAACTGAAA AACCAGCACA ACCATCTACT     1440

CCAAAAACAG GCTGGAAACA AGAAAACGGT ATGTGGTACT TCTACAATAC TGATGGTTCA     1500

ATGGCAACAG GATGGCTCCA AAACAACGGT TCATGGTACT ATCTAAACGC TAATGGTGCT     1560

ATGGCGACAG GATGGCTCCA AAACAATGGT TCATGGTACT ATCTAAACGC TAATGGTTCA     1620

ATGGCAACAG GATGGCTCCA AAACAATGGT TCATGGTACT ACCTAAACGC TAATGGTGCT     1680

ATGGCGACAG GATAG                                                     1695
```

(2) INFORMATION FOR SEQ ID NO:6:

(i) SEQUENCE CHARACTERISTICS:
        (A) LENGTH: 564 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Phe Ala Ser Lys Ser Glu Arg Lys Val His Tyr Ser Ile Arg Lys
1               5                   10                  15

Phe Ser Ile Gly Val Ala Ser Val Ala Val Ala Ser Leu Val Met Gly
                20                  25                  30

Ser Val His Ala Thr Glu Asn Glu Gly Ser Thr Gln Ala Ala Thr
            35                  40              45

Ser Ser Asn Met Ala Lys Thr Glu His Arg Lys Ala Lys Gln Val
        50                  55                  60

Val Asp Glu Tyr Ile Glu Lys Met Leu Arg Glu Ile Gln Leu Asp Arg
65                  70                  75                  80

Arg Lys His Thr Gln Asn Val Ala Leu Asn Ile Lys Leu Ser Ala Ile
                85                  90                  95

Lys Thr Lys Tyr Leu Arg Glu Leu Asn Val Leu Glu Glu Lys Ser Lys
                100                 105                 110

Asp Glu Leu Pro Ser Glu Ile Lys Ala Lys Leu Asp Ala Ala Phe Glu
            115                 120                 125

Lys Phe Lys Lys Asp Thr Leu Lys Pro Gly Glu Lys Val Ala Glu Ala
        130                 135                 140

Lys Lys Lys Val Glu Glu Ala Lys Lys Ala Glu Asp Gln Lys Glu
145                 150                 155                 160

Glu Asp Arg Arg Asn Tyr Pro Thr Asn Thr Tyr Lys Thr Leu Glu Leu
                165                 170                 175

Glu Ile Ala Glu Phe Asp Val Lys Val Lys Glu Ala Glu Leu Glu Leu
            180                 185                 190

Val Lys Glu Glu Ala Lys Glu Ser Arg Asn Glu Gly Thr Ile Lys Gln
        195                 200                 205

Ala Lys Glu Lys Val Glu Ser Lys Lys Ala Glu Ala Thr Arg Leu Glu
    210                 215                 220

Asn Ile Lys Thr Asp Arg Lys Lys Ala Glu Glu Glu Ala Lys Arg Lys
```

-continued

```
                225                 230                 235                 240
Ala Asp Ala Lys Leu Lys Glu Ala Asn Val Ala Thr Ser Asp Gln Gly
                    245                 250                 255
Lys Pro Lys Gly Arg Ala Lys Arg Gly Val Pro Gly Glu Leu Ala Thr
                260                 265                 270
Pro Asp Lys Lys Glu Asn Asp Ala Lys Ser Ser Asp Ser Ser Val Gly
                275                 280                 285
Glu Glu Thr Leu Pro Ser Ser Ser Leu Lys Ser Gly Lys Lys Val Ala
            290                 295                 300
Glu Ala Glu Lys Lys Val Glu Glu Ala Glu Lys Lys Ala Lys Asp Gln
305                 310                 315                 320
Lys Glu Glu Asp Arg Arg Asn Tyr Pro Thr Asn Thr Tyr Lys Thr Leu
                    325                 330                 335
Asp Leu Glu Ile Ala Glu Ser Asp Val Lys Val Lys Glu Ala Glu Leu
                340                 345                 350
Glu Ile Val Lys Glu Glu Ala Lys Glu Pro Arg Asp Glu Glu Lys Ile
            355                 360                 365
Lys Gln Ala Lys Ala Lys Val Glu Ser Lys Lys Ala Glu Ala Thr Arg
    370                 375                 380
Leu Glu Asn Ile Lys Thr Asp Arg Lys Lys Ala Glu Glu Glu Ala Lys
385                 390                 395                 400
Arg Lys Ala Ala Glu Glu Asp Lys Val Lys Glu Lys Pro Ala Glu Gln
                405                 410                 415
Pro Gln Pro Ala Pro Ala Thr Gln Pro Glu Lys Pro Ala Pro Lys Pro
                420                 425                 430
Glu Lys Pro Ala Glu Gln Pro Lys Ala Glu Lys Thr Asp Asp Gln Gln
                435                 440                 445
Ala Glu Glu Asp Tyr Ala Arg Arg Ser Glu Glu Glu Tyr Asn Arg Leu
    450                 455                 460
Thr Gln Gln Gln Pro Pro Lys Thr Glu Lys Pro Ala Gln Pro Ser Thr
465                 470                 475                 480
Pro Lys Thr Gly Trp Lys Gln Glu Asn Gly Met Trp Tyr Phe Tyr Asn
                485                 490                 495
Thr Asp Gly Ser Met Ala Thr Gly Trp Leu Gln Asn Asn Gly Ser Trp
                500                 505                 510
Tyr Tyr Leu Asn Ala Asn Gly Ala Met Ala Thr Gly Trp Leu Gln Asn
            515                 520                 525
Asn Gly Ser Trp Tyr Tyr Leu Asn Ala Asn Gly Ser Met Ala Thr Gly
            530                 535                 540
Trp Leu Gln Asn Asn Gly Ser Trp Tyr Tyr Leu Asn Ala Asn Gly Ala
545                 550                 555                 560
Met Ala Thr Gly
```

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GCACAACCAT CTACTCCA                                            18

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
GTACAGGAAT TCAGTATTAA CTA                                              23
```

(2) INFORMATION FOR SEQ ID NO:9:

(i) SEQUENCE CHARACTERISTICS:
        (A) LENGTH: 220 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Asp Arg Trp Lys Gln Glu Asn Gly Met Trp Tyr Phe Tyr Asn Thr Asp
1               5                   10                  15

Gly Ser Met Ala Thr Gly Trp Leu Gln Asn Asn Gly Ser Trp Tyr Tyr
            20                  25                  30

Leu Asn Ala Asn Gly Ala Met Ala Thr Gly Trp Leu Gln Asn Asn Gly
        35                  40                  45

Ser Trp Tyr Tyr Leu Asn Ala Asn Gly Ser Met Ala Thr Gly Trp Leu
50                  55                  60

Gln Asn Asn Gly Ser Trp Tyr Tyr Leu Asn Ala Asn Gly Ala Met Ala
65                  70                  75                  80

Thr Gly Leu Gln Tyr Asn Gly Ser Trp Tyr Tyr Leu Asn Ser Asn Gly
                85                  90                  95

Ala Met Ala Thr Gly Trp Leu Gln Tyr Asn Gly Ser Trp Tyr Tyr Leu
            100                 105                 110

Asn Ala Asn Gly Asp Met Ala Thr Gly Trp Leu Gln Asn Asn Gly Ser
        115                 120                 125

Trp Tyr Tyr Leu Asn Ala Asn Gly Asp Met Ala Thr Gly Trp Leu Gln
130                 135                 140

Tyr Asn Gly Ser Trp Tyr Tyr Leu Asn Ala Asn Gly Asp Met Ala Thr
145                 150                 155                 160

Gly Trp Val Lys Asp Gly Asp Thr Trp Tyr Tyr Leu Glu Ala Ser Gly
                165                 170                 175

Ala Met Lys Ala Ser Gln Trp Phe Lys Val Ser Asp Lys Trp Tyr Tyr
            180                 185                 190

Val Asn Gly Ser Gly Ala Leu Ala Val Asn Thr Thr Val Asp Gly Tyr
        195                 200                 205

Gly Val Asn Ala Asn Gly Glu Trp Thr Lys His Tyr
    210                 215                 220
```

(2) INFORMATION FOR SEQ ID NO:10:

(i) SEQUENCE CHARACTERISTICS:
        (A) LENGTH: 217 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Lys Gln Glu Asn Gly Met Trp Tyr Phe Tyr Asn Thr Asp Gly Ser Met
1               5                   10                  15

Ala Thr Gly Trp Leu Gln Asn Asn Gly Ser Trp Tyr Tyr Leu Asn Ala
            20                  25                  30

Asn Gly Ala Met Ala Thr Gly Trp Leu Gln Asn Asn Gly Ser Trp Tyr
            35                  40                  45

Tyr Leu Asn Ala Asn Gly Ser Met Ala Thr Gly Trp Leu Gln Asn Asn
        50                  55                  60

Gly Ser Trp Tyr Tyr Leu Asn Ala Asn Gly Ala Met Ala Thr Gly Trp
65                  70                  75                  80

Leu Gln Tyr Asn Gly Ser Trp Tyr Tyr Leu Asn Ser Asn Gly Ala Met
                85                  90                  95

Ala Thr Gly Trp Leu Gln Tyr Asn Gly Ser Trp Tyr Tyr Leu Asn Ala
            100                 105                 110

Asn Gly Asp Met Ala Thr Gly Trp Leu Gln Asn Asn Gly Ser Trp Tyr
            115                 120                 125

Tyr Leu Asn Ala Asn Gly Asp Met Ala Thr Gly Trp Leu Gln Tyr Asn
        130                 135                 140

Gly Ser Trp Tyr Tyr Leu Asn Ala Asn Gly Asp Met Ala Thr Gly Trp
145                 150                 155                 160

Val Lys Asp Gly Asp Thr Trp Tyr Tyr Leu Glu Ala Ser Gly Ala Met
                165                 170                 175

Lys Ala Ser Gln Trp Phe Lys Val Ser Asp Lys Trp Tyr Tyr Val Asn
            180                 185                 190

Gly Ser Gly Ala Leu Ala Val Asn Thr Thr Val Asp Gly Tyr Gly Val
            195                 200                 205

Asn Ala Asn Gly Glu Trp Thr Lys Pro
        210                 215

(2) INFORMATION FOR SEQ ID NO:11:

(i) SEQUENCE CHARACTERISTICS:
        (A) LENGTH: 220 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Leu Glu Thr Arg Asn Gly Met Trp Tyr Phe Tyr Asn Thr Asp Gly Ser
1               5                   10                  15

Met Ala Thr Gly Trp Leu Gln Asn Asn Gly Ser Trp Tyr Tyr Leu Asn
            20                  25                  30

Ser Asn Gly Ala Met Ala Thr Gly Trp Leu Gln Asn Asn Gly Ser Trp
            35                  40                  45

Tyr Tyr Leu Asn Ala Asn Gly Ser Met Ala Thr Gly Trp Leu Gln Asn
        50                  55                  60

Asn Gly Ser Trp Tyr Tyr Leu Asn Ala Asn Gly Ala Met Ala Thr Gly
65                  70                  75                  80

Trp Leu Gln Tyr Asn Gly Ser Trp Tyr Tyr Leu Asn Ser Asn Gly Ala
                85                  90                  95

Met Ala Thr Gly Trp Leu Gln Tyr Asn Gly Ser Trp Tyr Tyr Leu Asn
            100                 105                 110

-continued

```
Ala Asn Gly Asp Met Ala Thr Gly Trp Leu Gln Asn Asn Gly Ser Trp
            115                 120                 125

Tyr Tyr Leu Asn Ala Asn Gly Asp Met Ala Thr Gly Trp Leu Gln Tyr
    130                 135                 140

Asn Gly Ser Trp Tyr Tyr Leu Asn Ala Asn Gly Asp Met Ala Thr Gly
145                 150                 155                 160

Trp Val Lys Asp Gly Asp Thr Trp Tyr Tyr Leu Glu Ala Ser Gly Ala
                165                 170                 175

Met Lys Ala Ser Gln Trp Phe Lys Val Ser Asp Lys Trp Tyr Tyr Val
            180                 185                 190

Asn Gly Ser Gly Ala Leu Ala Val Asn Thr Thr Val Asp Gly Tyr Gly
            195                 200                 205

Val Asn Ala Asn Gly Glu Trp Thr Lys Pro Asn Ile
            210                 215                 220

(2) INFORMATION FOR SEQ ID NO:12:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Thr Gly Trp Lys Gln Glu Asn Gly Met Trp Tyr Phe Tyr Asn Thr Asp
1               5                   10                  15

Gly Ser Met Ala
            20
```